US009653691B2

(12) United States Patent
So et al.

(10) Patent No.: US 9,653,691 B2
(45) Date of Patent: May 16, 2017

(54) PHOSPHORESCENCE-SENSITIZING FLUORESCENCE MATERIAL SYSTEM

(71) Applicants: Woo-Young So, Richboro, PA (US); Jui-Yi Tsai, Newtown, NJ (US)

(72) Inventors: Woo-Young So, Richboro, PA (US); Jui-Yi Tsai, Newtown, NJ (US)

(73) Assignee: Universal Display Corporation, Ewing, NJ (US)

( * ) Notice: Subject to any disclaimer, the term of this patent is extended or adjusted under 35 U.S.C. 154(b) by 697 days.

(21) Appl. No.: 13/711,751

(22) Filed: Dec. 12, 2012

(65) Prior Publication Data

US 2014/0158993 A1 Jun. 12, 2014

(51) Int. Cl.
 *H01L 51/00* (2006.01)
 *C07F 15/00* (2006.01)
 *H01L 51/50* (2006.01)

(52) U.S. Cl.
 CPC ...... *H01L 51/0085* (2013.01); *C07F 15/0033* (2013.01); *H01L 51/009* (2013.01); *H01L 51/5012* (2013.01); *H01L 51/5016* (2013.01); *H01L 51/5028* (2013.01)

(58) Field of Classification Search
 None
 See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,512,493 A * | 4/1996 | Mathis et al. | 436/537 |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,310,360 B1 * | 10/2001 | Forrest et al. | 257/40 |
| 6,337,102 B1 | 1/2002 | Forrest et al. | |
| 6,468,819 B1 | 10/2002 | Kim et al. | |
| 6,528,187 B1 | 3/2003 | Okada | |
| 6,645,645 B1 * | 11/2003 | Adachi et al. | 428/690 |
| 6,687,266 B1 | 2/2004 | Ma et al. | |
| 6,921,915 B2 | 7/2005 | Takiguchi et al. | |
| 7,090,928 B2 | 8/2006 | Thompson et al. | |
| 7,154,114 B2 | 12/2006 | Brooks et al. | |
| 7,230,107 B1 | 6/2007 | Herron et al. | |
| 7,232,618 B2 | 6/2007 | Yamada et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,498,437 B2 * | 3/2009 | Yang et al. | 546/4 |
| 7,534,505 B2 | 5/2009 | Lin et al. | |
| 7,655,323 B2 | 2/2010 | Walters et al. | |
| 7,968,146 B2 | 6/2011 | Wagner et al. | |
| 2001/0015432 A1 | 8/2001 | Igarashi | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0051449 A1 * | 3/2004 | Klausmann | H01L 51/5237 313/512 |
| 2004/0115476 A1 | 6/2004 | Oshiyama et al. | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |

(Continued)

FOREIGN PATENT DOCUMENTS

| | | |
|---|---|---|
| EP | 650955 | 5/1995 |
| EP | 1725079 | 11/2006 |
| EP | 1841834 | 10/2007 |
| EP | 2034538 | 3/2009 |
| EP | 2350216 | 8/2011 |
| JP | 2007123392 | 5/2007 |
| JP | 2007254297 | 10/2007 |
| JP | 2008074939 | 4/2008 |
| WO | WO 2004/093207 | 10/2004 |
| WO | WO 2004/107822 | 12/2004 |

(Continued)

OTHER PUBLICATIONS

Baldo et al. "High-efficiency fluorescent organic light-emitting devices using a phosphorescent sensitizer" Nature, vol. 403, 2000, 750-752.*
Harriman et al. "Length Dependence for Intramolecular Energy Transfer in Three- and Four-Color Donor-Spacer-Acceptor Arrays" J. Am. Chem. Soc. 2009, 131, 13375-13386.*
Guldi et al. "Intramolecular Electron Transfer in Fullerene/Ferrocene Based Donor-Bridge-Acceptor Dyads" J. Am. Chem. Soc. 1997, 119, 974-980.*

(Continued)

*Primary Examiner* — Robert S Loewe
(74) *Attorney, Agent, or Firm* — Morris & Kamlay LLP

(57) ABSTRACT

Novel molecules are provided that include a sensitizer group, an acceptor group, and an electron-transfer barrier that suppresses triplet-triplet energy transfer between the sensitizer group and the acceptor group. Organic light emitting devices (OLEDs) that include a layer including these novel molecules are also provided. These devices may be used to provide highly efficient OLEDs with longer operational lifetime.

23 Claims, 4 Drawing Sheets

(56) References Cited

U.S. PATENT DOCUMENTS

| | | | |
|---|---|---|---|
| 2005/0112407 A1 | 5/2005 | Ogasawara et al. | |
| 2005/0123751 A1 | 6/2005 | Tsutsui et al. | |
| 2005/0238919 A1 | 10/2005 | Ogasawara | |
| 2005/0244673 A1 | 11/2005 | Satoh et al. | |
| 2005/0247911 A1* | 11/2005 | Burn et al. | 252/301.35 |
| 2005/0260441 A1 | 11/2005 | Thompson et al. | |
| 2006/0008670 A1 | 1/2006 | Lin et al. | |
| 2006/0121308 A1 | 6/2006 | Katoh et al. | |
| 2006/0127696 A1 | 6/2006 | Stossel et al. | |
| 2006/0182992 A1 | 8/2006 | Nii et al. | |
| 2006/0194073 A1* | 8/2006 | Okada | 428/690 |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0057263 A1* | 3/2007 | Kahen | 257/79 |
| 2007/0087321 A1 | 4/2007 | Pribenszky et al. | |
| 2007/0103060 A1 | 5/2007 | Itoh et al. | |
| 2007/0111026 A1 | 5/2007 | Deaton et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0075973 A1* | 3/2008 | Kim et al. | 428/690 |
| 2008/0102310 A1* | 5/2008 | Thompson et al. | 428/690 |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0261076 A1 | 10/2008 | Kwong et al. | |
| 2008/0280163 A1* | 11/2008 | Kwong et al. | 428/704 |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0066238 A1* | 3/2009 | Chen et al. | 313/504 |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2009/0302743 A1 | 12/2009 | Kato et al. | |
| 2009/0309488 A1 | 12/2009 | Kato et al. | |
| 2010/0012931 A1 | 1/2010 | Kato et al. | |
| 2010/0084966 A1 | 4/2010 | Otsu et al. | |
| 2010/0090591 A1 | 4/2010 | Alleyne et al. | |
| 2010/0148663 A1 | 6/2010 | Tsai et al. | |
| 2010/0187984 A1 | 7/2010 | Lin et al. | |
| 2010/0244004 A1 | 9/2010 | Xia et al. | |
| 2010/0295032 A1 | 11/2010 | Kwong et al. | |
| 2011/0057171 A1* | 3/2011 | Adamovich et al. | 257/40 |
| 2011/0057559 A1 | 3/2011 | Xia et al. | |
| 2011/0163302 A1 | 7/2011 | Lin et al. | |
| 2011/0204333 A1 | 8/2011 | Xia et al. | |
| 2013/0261098 A1* | 10/2013 | Pan et al. | 514/185 |

FOREIGN PATENT DOCUMENTS

| | | |
|---|---|---|
| WO | WO 2005/014551 | 2/2005 |
| WO | WO 2005/019373 | 3/2005 |
| WO | WO 2005/030900 | 4/2005 |
| WO | WO 2005/089025 | 9/2005 |
| WO | WO 2005/123873 | 12/2005 |
| WO | WO 2006/009024 | 1/2006 |
| WO | WO 2006/056418 | 6/2006 |
| WO | WO 2006/072002 | 7/2006 |
| WO | WO 2006/082742 | 8/2006 |
| WO | WO 2006/098120 | 9/2006 |
| WO | WO 2006/100298 | 9/2006 |
| WO | WO 2006/103874 | 10/2006 |
| WO | WO 2006/114966 | 11/2006 |
| WO | 2006/132173 | 12/2006 |
| WO | 2007/002683 | 1/2007 |
| WO | 2007/004380 | 1/2007 |
| WO | 2007/063754 | 6/2007 |
| WO | 2007/063796 | 6/2007 |
| WO | 2008/056746 | 5/2008 |
| WO | 2008057394 | 5/2008 |
| WO | 2008/101842 | 8/2008 |
| WO | 2008/132085 | 11/2008 |
| WO | 2009/000673 | 12/2008 |
| WO | 2009/003898 | 1/2009 |
| WO | 2009/008311 | 1/2009 |
| WO | 2009/018009 | 2/2009 |
| WO | 2009/021126 | 2/2009 |
| WO | 2009/050290 | 4/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 2009/100991 | 8/2009 |
| WO | 2010011390 | 1/2010 |
| WO | 2010/028151 | 3/2010 |
| WO | 2010/056066 | 5/2010 |
| WO | 2010/079051 | 7/2010 |
| WO | 2010/086089 | 8/2010 |
| WO | 2010/107244 | 9/2010 |
| WO | 2011/044988 | 4/2011 |
| WO | 2011/051404 | 5/2011 |
| WO | 2011/075644 | 6/2011 |
| WO | 2011/086863 | 7/2011 |
| WO | WO 2012079673 A1 * 6/2012 ............ C09K 11/06 |  |

OTHER PUBLICATIONS

Hudson et al. "Switchable Ambient-Temperature Singlet-Triplet Dual Emission in Nonconjugated Donor-Acceptor Triarylboron-Pt(II) Complexes" Chem. Eur. J. 2009, 15, 6131-6137.*

Leroy-Lhez et al. "Perylenediimide derivatives in new donor-acceptor dyads" C. R. Chemie 9, 2006, 240-246.*

Clapp et al. "Can Luminescent Quantum Dots be Efficient Energy Acceptors with Organic Dye Donors?" J. Am. Chem. Soc. 2005, 127, 1242-1250.*

Montes et al. "Molecular-Wire Behavior of OLED Materials: Exciton Dynamics in Multichromophoric Alq3-Oligofluorene-Pt(II)porplyrin Triads" J. Am. Chem. Soc. 2006, 128, 12436-12438.*

Freys et al. "Supramolecular and Intramolecular Energy Transfer with Ruthenium-Anthracene Donor-Acceptor Couples: Salt Bridge versus Covalent Bond" Eur. J. Inorg. Chem. 2010, 5509-5516.*

Hankache et al. "Photoinduced Electron Transfer in Linear Triarylamine-Photosensitizer-Anthraquinone Triads with Ruthenium(II), Osmium(II), and Iridium(III)" Inorg. Chem. 2012, 51, 6333-6344.*

Bieri et al. "The speed limit for protein folding measure by triplet-triplet energy transfer" Proc. Natl. Acad. Sci. USA 1999, 96, 9597-9601.*

Closs et al. "A Connection between Intramolecular Long-Range Electron, Hole, and Triplet Energy Transfers" J. Am. Chem. Soc. 1989, 111, 3751-3753.*

Harriman et al. "An Unusually Shallow Distance-Dependence for Triplet-Energy Transfer" Angew. Chem. Int. Ed. 2000, 39(23), 4287-4290.*

Zhao et al. "Triplet-triplet annihilation based upconversion: from triplet sensitizers and triplet acceptors to upconversion quantum yields" RSC Advances, 2011, 1, 937-950.*

Adachi et al., "High-efficiency red electrophosphorescence devices", Applied Physics Letters, vol. 78, No. 11, Mar. 12, 2001.

Adachi et al., "Nearly 100% internal phosphorescence efficiency in an organic light emitting device", Journal of Applied Physics, vol. 90, No. 10, Nov. 15, 2001.

Adachi et al., "Organic electroluminescent device having a hole conductor as an emitting layer", Applied Physics Letters, vol. 55, Oct. 9, 1989.

(56) References Cited

OTHER PUBLICATIONS

Aonuma et al., "Material design of hole transport materials capable of thick-filim formation in organic light emitting diodes", Applied Physics Letters, vol. 90, 2007.
Baldo et al., "Highly efficient phosphorescent emission from organic electroluminescent devices", Nature, vol. 395, pp. 151-154, 1998.
Baldo et al., "Very high-efficiency green organic light-emitting devices based on electrophosphorescence", Applied Physics Letter, vol. 75, No. 1, pp. 4-6, 1999.
Chang et al., "Highly Efficient Blue-Emitting Iridium(III) Carbene Complexes and Phosphorescent OLEDs", Angew. Chem. Int. Ed. 47, pp. 4542-4545, 2008.
Gao et al., "Bright-blue electroluminescence from a silyl-substituted ter-(phenylene-vinylene) derivative", Applied Physics Letters, vol. 74, No. 6, Feb. 8, 1999.
Guo et al., "Highly efficient electrophosphorescent polymer light-emitting devices", Organic Electronics 1, pp. 15-20, 2000.
Hamada et al., "High Luminance in Organic Electroluminescent Devices with Bis(10-hydroxybenzo[h]quinolinato)beryllium as an Emitter", Chemistry Letters, pp. 905-906, 1993.
Holmes et al., "Blue organic electrophosphorescence using exothermic host-guest energy transfer", Applied Physics Letters, vol. 82, No. 15, Apr. 14, 2003.
Hu et al., "Novel high Tg hole-transport molecules based on indolo[3,2-b ]carbazoles for organic light-emitting devices", Synthetic Metals 111-112, pp. 421-424, 2000.
Huang et al., "Highly Efficient Red-Emission Polymer Phosphorescent Light-Emitting Diodes Based on Two Novel Tris(I-phenylisoquinolinato-C2,N)iridium(III) Derivatives", Advanced Materials, No. 19, 2007.
Huang et al., "Highly Phosphorescent Bis-Cyclometalated Iridium Complexes Containing Benzoimidazole-Based Ligands", Chemistry of Materials, vol. 16, 2004.
Hung et al., "Anode modification in organic light-emitting diodes by low-frequency plasma polymerization of CHF3", Applied Physics Letters, vol. 78, No. 5, Jan. 29, 2001.
Ikeda et al., "P-185: Low-Drive-Voltage OLEDs with a Buffer Layer Having Molybdenum Oxide", Society for Information Display Digest, pp. 923-926, 2006.
Kanno et al., "Highly efficient and stable red phosphorescent organic light-emitting device using bis[2-(2-benzothiazoyl)phenolato]zinc(II) as host material", Applied Physics Letters, vol. 90, 2007.
Kido et al., "1,2,4-Triazole Derivative as an Electron Transport Layer in Organic Electroluminescent Devices", Japanese Journal of Applied Physics, vol. 32, pp. L 917-L 920 Part 2, No. 7A, Jul. 1, 1993.
Kuwabara et al., "Thermally Stable Multilayered Organic Electroluminescent Devices Using Novel Starburst Molecules, 4,4' ,4"-Tri(N-carbazolyl)triphenylamine (TCTA) and 4,4' ,4"-Tris(3-methylphenylphenylamino) triphenylamine (m-MTDATA), as Hole-Transport Materials", Advanced Materials, 6, No. 9, 1994.
Kwong et al., "High operational stability of electrophosphorescent devices", Applied Physics Letters, vol. 81, No. 1, Jul. 1, 2002.
Lamansky et al., "Synthesis and Characterization of Phosphorescent Cyclometalated Iridium Complexes", Inorganic Chemistry, vol. 40, No. 7, 2001.
Lee et al., "Polymer phosphorescent light-emitting devices doped with tris(2-phenylpyridine) iridium as a triplet emitter", Applied Physics Letters, vol. 77, No. 15, Oct. 9, 2000.
Lkai et al., "Highly efficient phosphorescence from organic light-emitting devices with an exciton-block layer", Applied Physics Letters, vol. 79, No. 2, Jul. 9, 2001.
Lnada et al., "1,3,5-Tris[4-(diphenylamino)phenyl]benzene and its Methyl substituted Derivatives as a Novel Class of Amorphous Molecular Materials", Journal of Materials Chemistry, vol. 3, 1993.
Lo et al., "Blue Phosphorescence from Iridium(III) Complexes at Room Temperature", Chemistry of Materials, vol. 18, 2006.

Ma et al., "Triplet luminescent dinuclear-gold complex-based light-emitting diodes with low turn-on voltage", Applied Physics Letters, vol. 74, No. 10, Mar. 8, 1999.
Mi et al., "Thermally Stable Hole-Transporting Material for Organic Light-Emitting Diode: an Isoindole Derivative", Chemistry of Materials, vol. 15, 2003.
Nishida et al., "Preparation, Characterization, and Electroluminescence Characteristics of a-Diimine-type Platinum(II) Complexes with Perfluorinated Phenyl Groups as Ligands", Chemistry Letters, vol. 34, No. 4, 2005.
Niu et al., "Highly Efficient Electrophosphorescent Devices with Saturated Red Emission from a Neutral Osmium Complex", Chemistry of Materials, vol. 17, 2005.
Noda et al., "5,5'-Bis(dimesitylbory1)-2,2'-bithiophene and 5,5"-Bis(dimesitylboryl)-2,2':5',2"-terthiophene as a Novel Family of Electron-Transporting Amorphous Molecular Materials", Journal of the American Chemical Society, vol. 120, No. 37, 1998.
Okumoto et al., "Green fluorescent organic light-emitting device with external quantum efficiency of nearly 10%", Applied Physics Letters, vol. 89, 2006.
Ostergard et al., "Langmuir-Blodgett light-emitting diodes of poly(3-hexylthiophene): electro-optical characteristics related to structure", Synthetic Metals 88, pp. 171-177, 1997.
Palilis et al., "High efficiency molecular organic light-emitting diodes based on silole derivatives and their exciplexes", Organic Electronics 4, pp. 113-121, 2003.
Ranjan et al., "Realizing Green Phosphorescent Light-Emitting Materials from Rhenium(I) Pyrazolato Diimine Complexes", Inorganic Chemistry, vol. 42, No. 4, 2003.
Sakamoto et al., "Synthesis, Characterization, and Electron-Transport Property of Perfluorinated Phenylene Dendrimers", Journal of the American Chemical Society, vol. 122, No. 8, 2000.
Salbeck et al., "Low molecular organic glasses for blue electroluminescence", Synthetic Metals 91, pp. 209-215, 1997.
Shirota et al., "Starburst molecules based on pi-electron systems as materials for organic electroluminescent devices", Journal of Luminescence 72-74, pp. 985-991, 1997.
Sotoyama et al., "Efficient organic light-emitting diodes with phosphorescent platinum complexes containing N^ C^ N-coordinating tridentate ligand", Applied Physics Letters, vol. 86, 2005.
Sun et al., "High-efficiency white organic light emitting devices with three separate phosphorescent emission layers", Applied Physics Letters, vol. 91, 2007.
Takizawa et al., "Phosphorescent Iridium Complexes Based on 2-Phenylimidazo[1 ,2-a]pyridine Ligands: Tuning of Emission Color toward the Blue Region and Application to Polymer Light-Emitting Devices", Inorganic Chemistry, vol. 46, No. 10, 2007.
Tang et al., "Organic electroluminescent diodes", Applied Physics Letters, No. 51, Sep. 21, 1987.
Tung et al., "Highly Efficient Red Phosphorescent Osmium(II) Complexes for OLED Applications", Organometallics, 23, pp. 3745-3748, 2004.
Tung et al., "Organic Light-Emitting Diodes based on Charge-Neutral Ru Phosphorescent Emitters", Advanced Materials, 17, No. 8, Apr. 18, 2005.
Van Slyke et al., "Organic electroluminescent devices with improved stability", Applied Physics Letters, 69 (15), Oct. 7, 1996.
Wang et al., "Highly efficient electroluminescent materials based on fluorinated organometallic iridium compounds", Applied Physics Letters, vol. 79, No. 4, Jul. 23, 2001.
Wong et al., "A novel class of phosphorescent gold(III) alkynyl-based organic light-emitting devices with tunable colour", Chemical Communications, Royal Society of Chemistry, p. 2906-2908, 2005.
Wong et al., "Multifunctional Iridium Complexes Based on Carbazole Modules as Highly Efficient Electrophosphors", Angewandte Chemie, Int. Ed., No. 45, 2006.
Zhao et al., "Triplet-triplet annihilation based upconversion: from triplet sensitizers and triplet acceptors to upconversion quantum yields", Royal Society of Chemistry Advances, 1, pp. 937-950, Oct. 5, 2011.

* cited by examiner (A)

(B)

(C)

PHOSPHORESCENCE-SENSITIZING FLUORESCENCE MATERIAL SYSTEM

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs) and materials for use therein. More specifically, it relates to devices and compounds that include a sensitizer group, an acceptor group, and an electron-transfer barrier that suppresses triplet-triplet energy transfer between the sensitizer group and the acceptor group.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)3, which has the following structure:

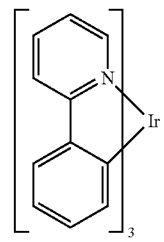

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Devices and materials that make use of or provide triplet-singlet Forster resonant energy transfer to convert energy from an exciton formation source to an energy state with longer wavelength emission are provided. These materials are to be used as active electroluminescent materials in OLEDs.

In an aspect, molecules are provided which comprise a sensitizer group, an acceptor group, and an electron-transfer barrier that suppresses triplet-triplet energy transfer between the sensitizer group and the acceptor group. In an aspect, the maximum length of the electron-transfer barrier is less than about 10 nm, and preferably less than about 8 nm.

In an aspect, the sensitizer group comprises a phosphorescent compound. In an aspect, the sensitizer group comprises a metal complex.

In an aspect, the acceptor group comprises a fluorescent emitting compound. In an aspect, the acceptor group comprises a poly-aromatic compound. In an aspect, the acceptor group comprises a quantum dot.

In an aspect, the electron-transfer barrier is disposed at least partially between the sensitizer group and the acceptor group. In an aspect, the electron-transfer barrier substantially surrounds the acceptor group. In an aspect, the electron-transfer barrier substantially surrounds the sensitizer group.

In an aspect, a device comprising an organic layer including a molecule as described above is provided. In an aspect, the device comprises an OLED. In an aspect, the device further comprises an anode and a cathode, and the organic layer is disposed between the anode and the cathode. In an aspect, the device further comprises a touch sensitive surface.

In an aspect, the device comprises a device type selected from the group consisting of: a full-color display, a flexible display in a consumer device, a mobile phone, a pad computer, a smartphone, a portable computer, a monitor, a television, and a consumer device including a flexible display.

In an aspect, the device further comprises a thin film encapsulation layer disposed over or under the OLED.

In an aspect, the device comprises an active matrix backplane.

In an aspect, molecules for organic electroluminescent devices are provided. The molecules comprise a phosphorescent sensitizer group, a fluorescent acceptor group, and an electron-transfer barrier. In an aspect, the molecule has the following general structure:

wherein S is a phosphorescent sensitizer group; n is an integer value of 1 or greater; B is an electron-transfer barrier selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, ester, and combinations thereof; m is an integer value of 1 or greater; A is a fluorescent acceptor selected from the group consisting of fluorescent emitting compounds, polycyclic aromatic compounds, naphthalene, anthracene, tetracene, triphylene, pyrene, chrysene, and perylene, and y is an integer value of 1 or greater.

In an aspect, the phosphorescent sensitizer group is a transition metal complex, the transition metal complex having at least one ligand or part of a ligand if the ligand is more than bidentate selected from the group consisting of:

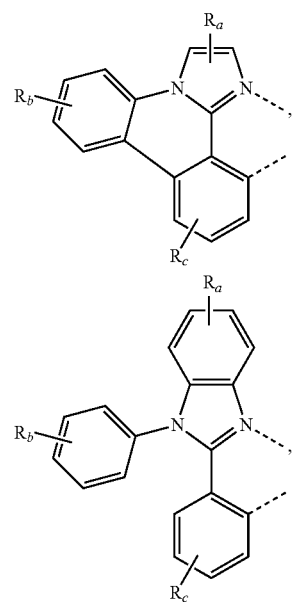

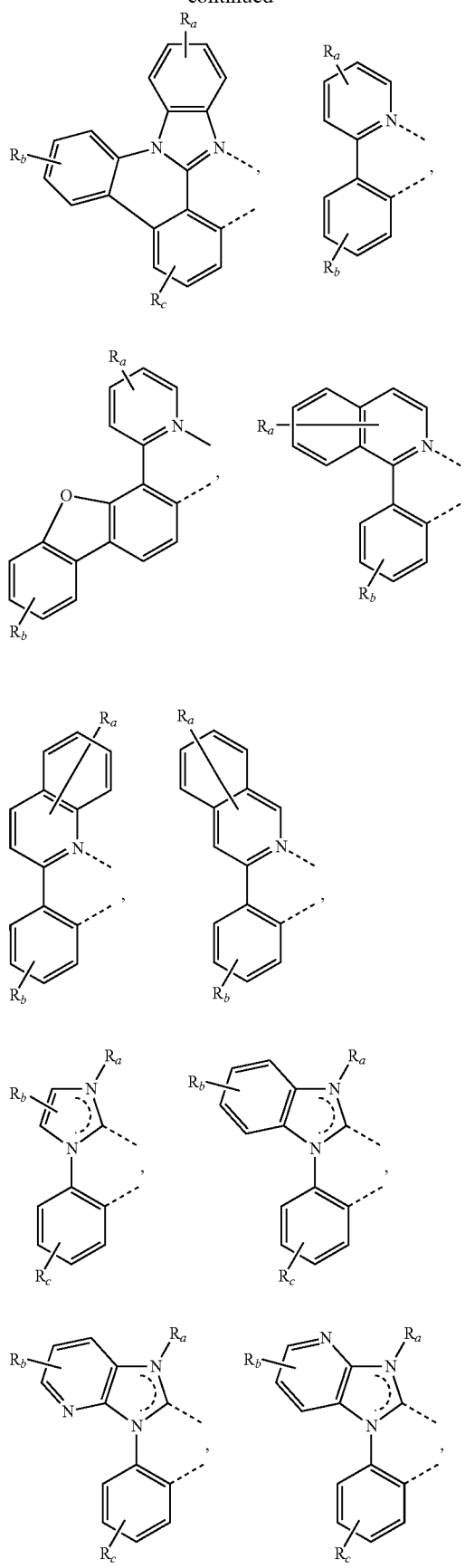
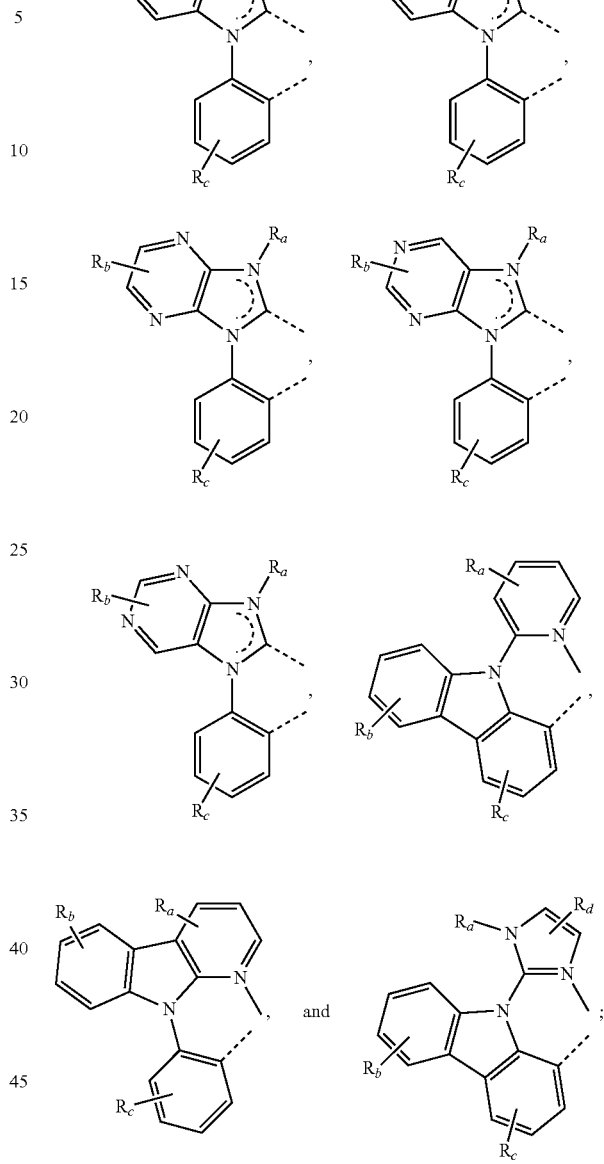

wherein $R_a$, $R_b$, $R_c$, and $R_d$ may represent mono, di, tri, or tetra substitution, or no substitution; wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of $R_a$, $R_b$, $R_c$, and $R_d$ are optionally joined to form a fused ring or form a multidentate ligand.

In an aspect, a device comprising an organic layer comprising a compound described above is provided.

In an aspect, a compound is selected from the group consisting of:

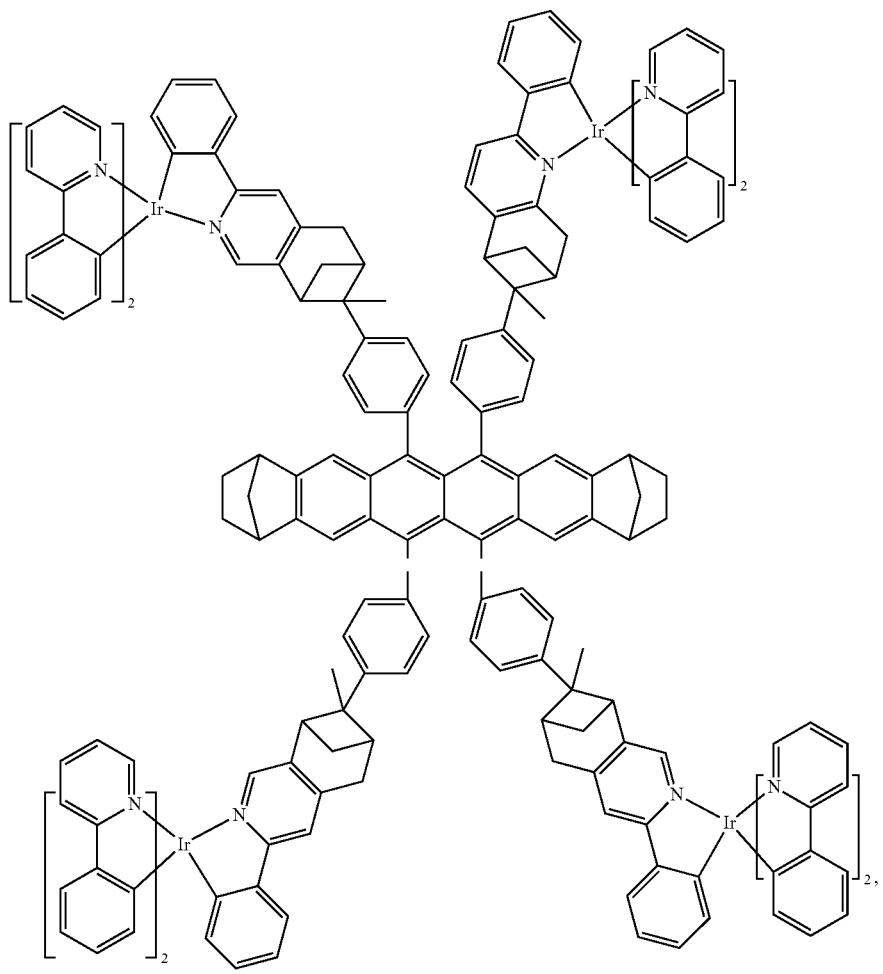
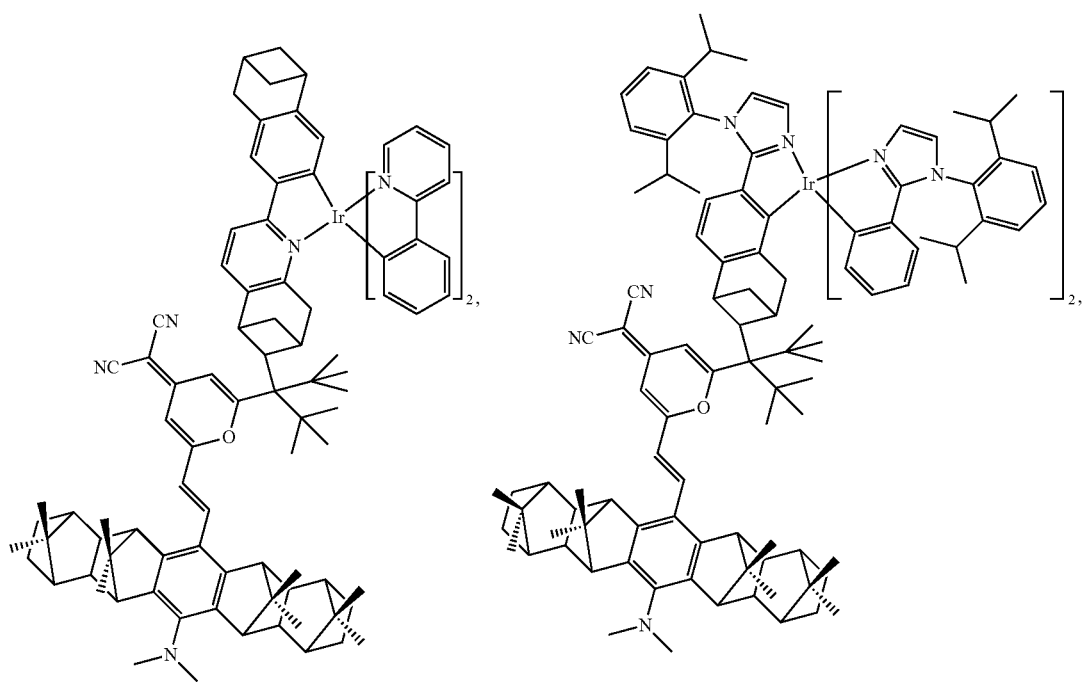

-continued
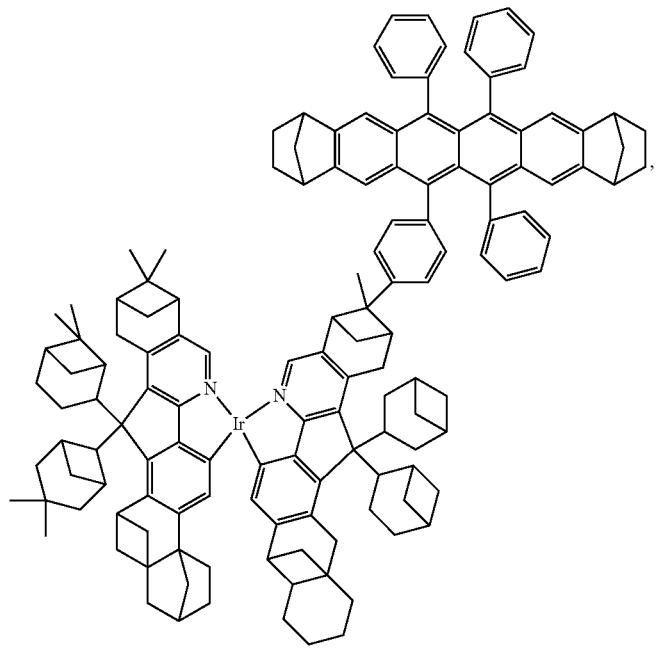
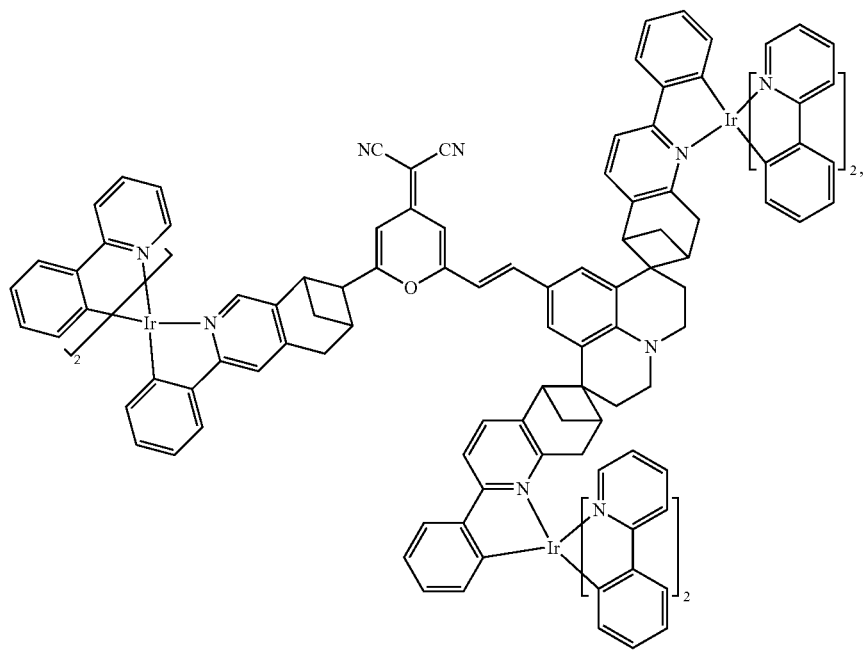

-continued

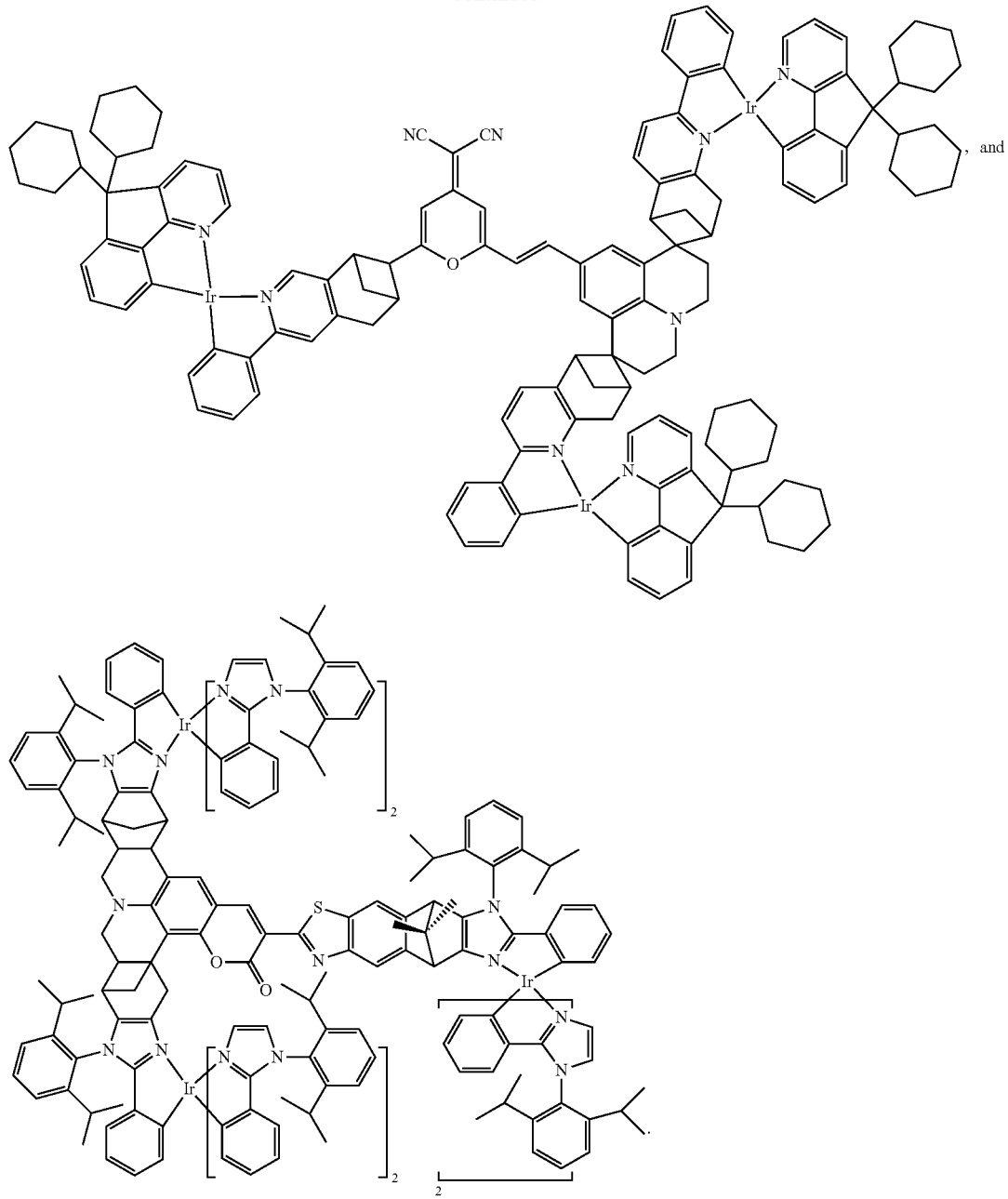

In an aspect, an organic light emitting device is provided, the device comprising an anode, a cathode, and an organic layer, disposed between the anode and the cathode, the organic layer comprising a compound as described above.

In an aspect, an organic light emitting device is provided. The device includes an anode, a cathode, and an organic emissive layer disposed between the anode and the cathode. In an aspect, the organic emissive layer includes a host and a phosphorescent dopant. In an aspect, the organic emissive layer includes a molecule as described above.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
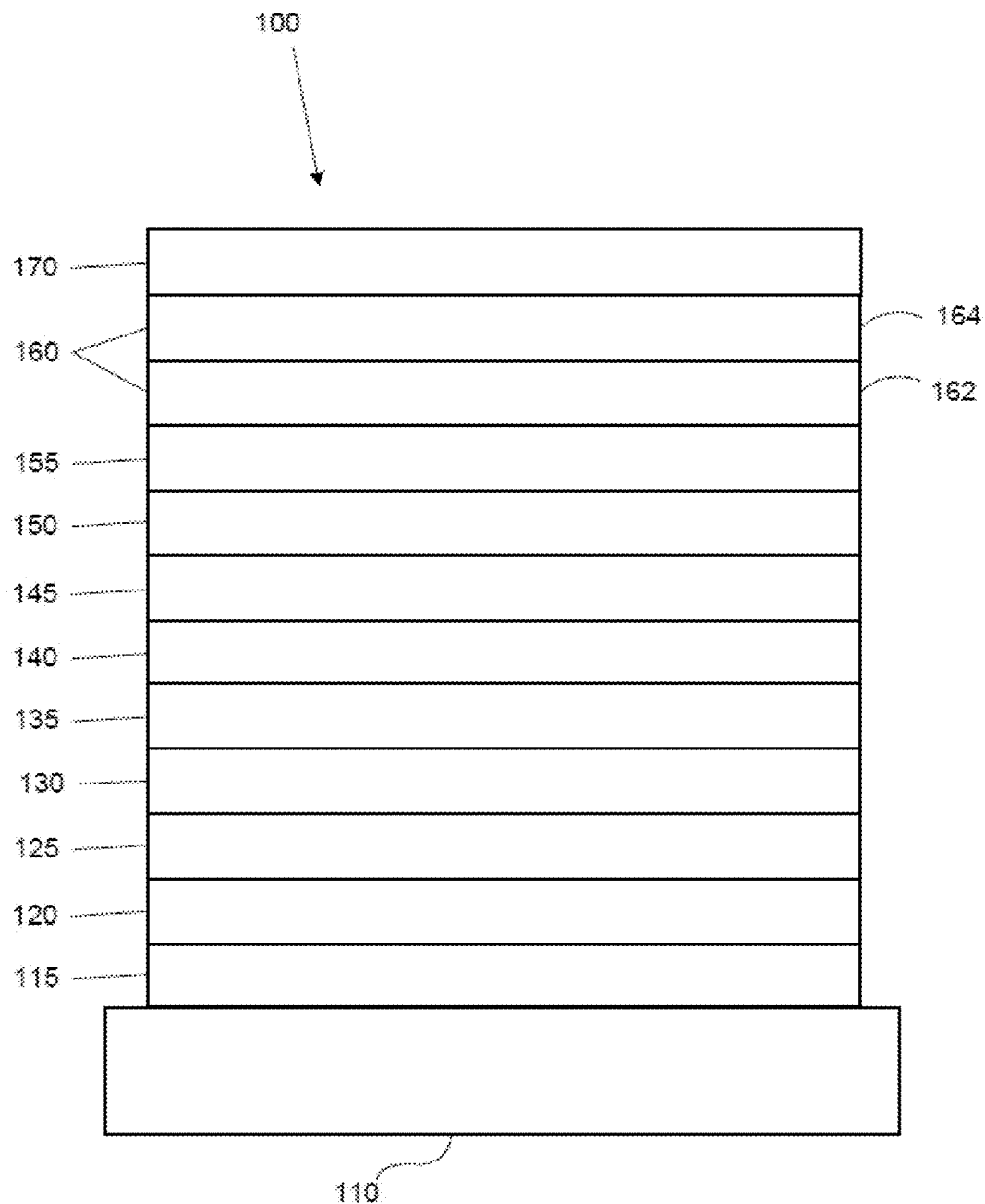
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
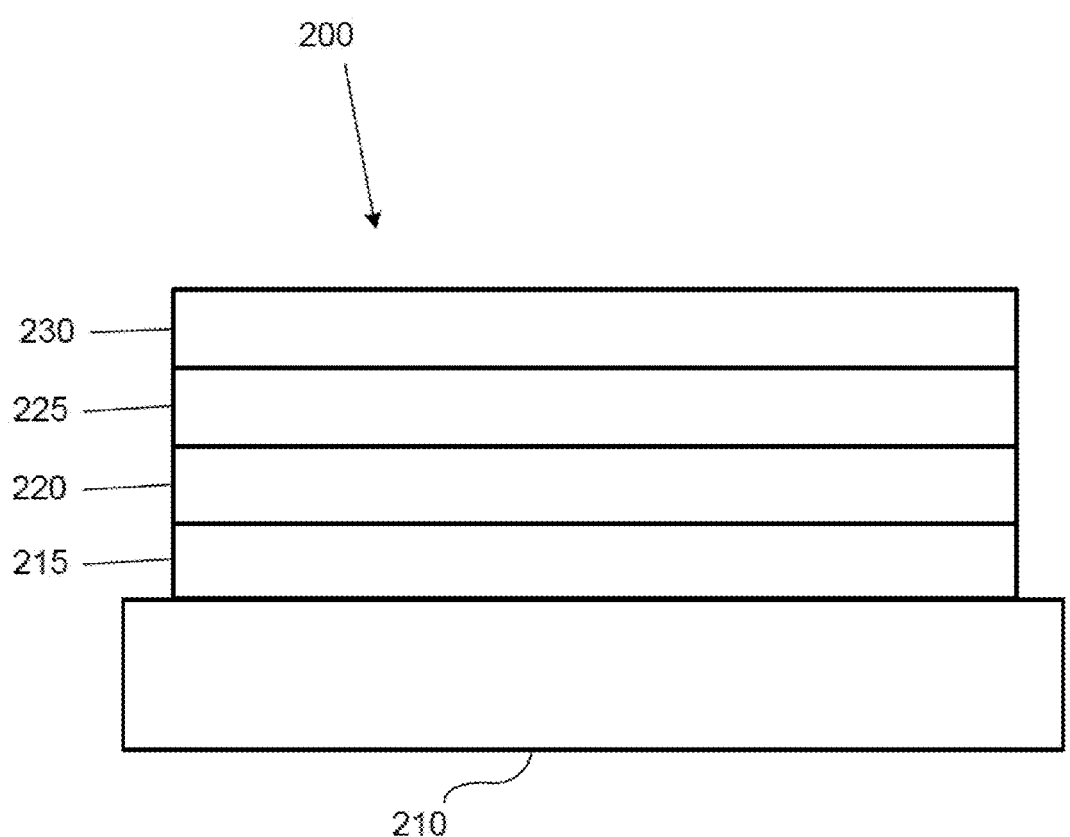
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In general, phosphorescence-sensitized fluorescence material systems are governed by two resonant energy transfer mechanisms, Forster and Dexter energy transfer. Forster energy transfer is a longer-range process than Dexter energy transfer. Further, Dexter energy transfer provides the direct exchange of electrons between a sensitizer group and an acceptor group, whereas Forster energy transfer requires columbic interactions. In a conventional sensitizing system, the triplet energy of the fluorescent compound is normally lower than the phosphorescent sensitizer. Triplet-to-triplet Dexter energy transfer typically leads to an exciton quenching process in the fluorescence material. This exciton quenching process can make it difficult to achieve high efficiency phosphorescence-sensitized fluorescence systems. (See FIG. 3(A)).

Figure 3:
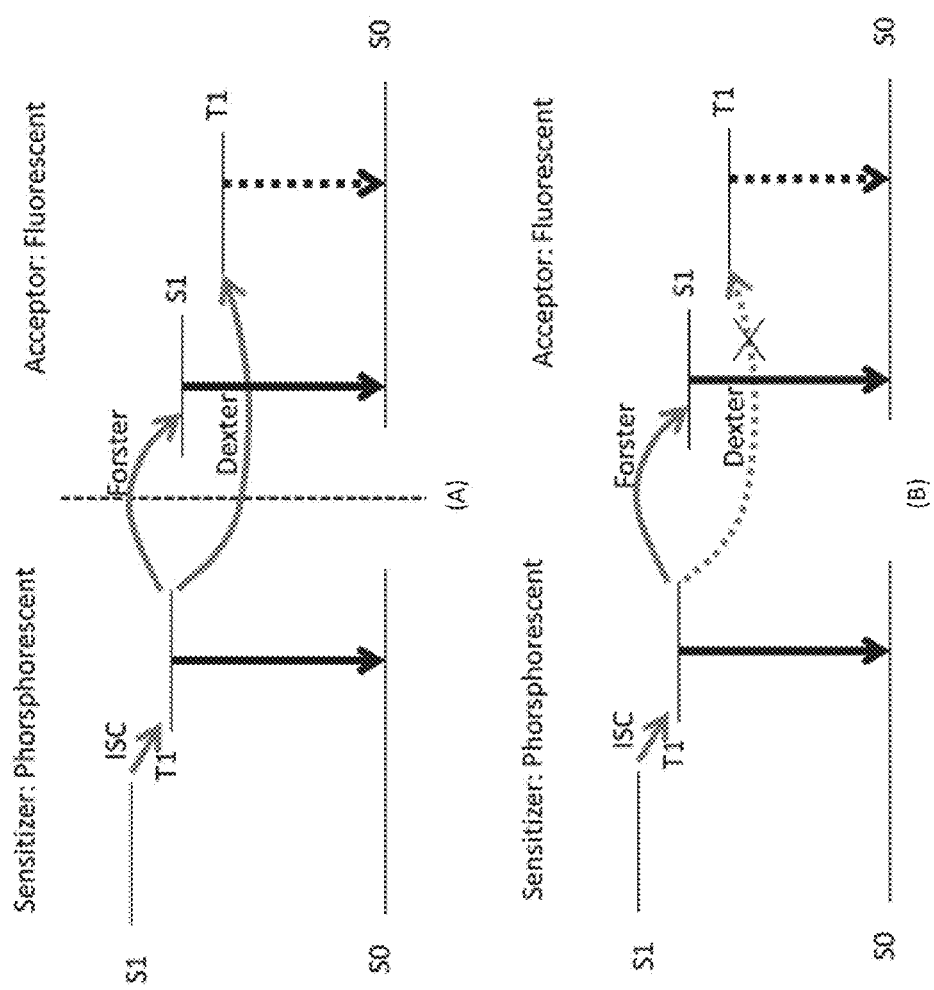
FIG. 3 shows a comparative diagram of a conventional phosphorescent-sensitized fluorescent system and phosphorescent-sensitized fluorescent system having an electron-transfer barrier for preventing Dexter energy transfer.

Referring to FIG. 3, diagram (A) shows a conventional phosphorescent-sensitized fluorescent system. In a conventional phosphorescent-sensitized fluorescent system, when phosphorescent materials sensitize fluorescent materials in a conventional co-doped system, Forster energy transfer rate can be enhanced by reducing the distance between the sensitizer group and the acceptor group. However, Dexter energy transfer rate can also be enhanced, even more strongly dependent on the distance, which can result in a significant increase in energy transfer rate into the non-radiation triplet states in the fluorescence material. In this case, the radiationless triplet sites act as quenching sites in the acceptor.

Molecular structures for TTA-UC have been described in the art. For example, in Zhao, Jianzhang, et al, Royal Society of Chemistry, 2011, 1(6), 937-950, Ru(II) polyimine complexes, Pt(II)/Pd(II) porphyrin complexes, Pt(II) acetylide complexes, Pt(II) bisacetylide complexes, and various acceptors were provided. By linking the triplet donor and fluorescent dye with a conjugated moiety, the TTET (Dexter) process was enhanced. Furthermore, these structures did not provide an electron transfer barrier, nor was such a mechanism contemplated.

The present invention enhances energy transfer from the sensitizer to the acceptor, in part, due to a relatively short distance between the sensitizer and the acceptor, while an electron-transfer barrier reduces non-radiative quenching between the sensitizer and the acceptor. In particular, the molecules described herein include an electron-transfer barrier to hinder the exchange of electrons between the sensitizer and acceptor. This electron-transfer barrier results in suppression of Dexter energy transfer while keeping Forster energy transfer unchanged. Further, molecules and molecular structures are provided herein comprising a single molecule that is composed of two building blocks of a sensitizer and an acceptor in relatively close proximity to each other. Because energy transfer is a function of distance, the proximity of the sensitizer and the acceptor to each other promotes energy transfer between them.

Referring to FIG. 3, diagram (B) shows a phosphorescent-sensitized fluorescent system based on the molecules provided herein. In arrangements described herein, a relatively short distance between a sensitizer group and an acceptor group in a single molecule may be used to enhance Forster and Dexter energy transfer, while an electron barrier prevents the exciton quenching process by suppressing Dexter energy transfer. (See FIG. 3(B) and FIG. 4).

In an aspect of the invention, molecules are provided which include a sensitizer group, an acceptor group, and an electron-transfer barrier that suppresses triplet-triplet energy transfer between the sensitizer group and the acceptor group. In an aspect of the invention, the sensitizer group may comprise a phosphorescent compound, for example a metal complex. The acceptor group may comprise a fluorescent compound, for example, a poly-aromatic compound.

In some embodiments, the electron-transfer barrier may have a maximum length between the sensitizer group and the acceptor group of less than about 10 nm, and preferably less than about 8 nm. As used herein, the length of the electron-transfer barrier refers to the direct distance between the atom center which bonds to the sensitizer group and the atom center which bonds to the acceptor group. Additionally, the electron-transfer barrier may be disposed at least partially between the sensitizer group and the acceptor group. The electron-transfer barrier may substantially surround the acceptor group or the sensitizer group. In this embodiment, the electron-transfer barrier is covalently bound to the acceptor group and/or the sensitizer group. Accordingly, the acceptor group or the sensitizer group may be isolated by the electron-transfer barrier. Thus, the electron-transfer barrier prevents the acceptor group and/or the sensitizer group from contacting adjacent molecules.

As used herein, one group may be said to "substantially surround" another when it is isolated by the other group. For example, the sensitizer group and/or the acceptor group may be isolated by the electron-transfer barrier, such that the electron-transfer barrier prevents the sensitizer group and/or the acceptor group from contacting adjacent molecules.

Figure 4:
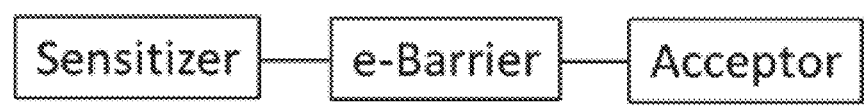
FIG. 4 shows exemplary molecular design block diagrams of molecules provided herein.
Figure 4:
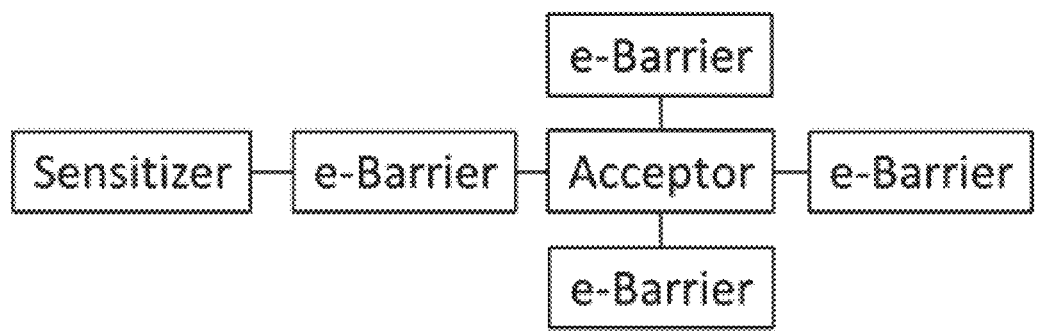
Figure 4:
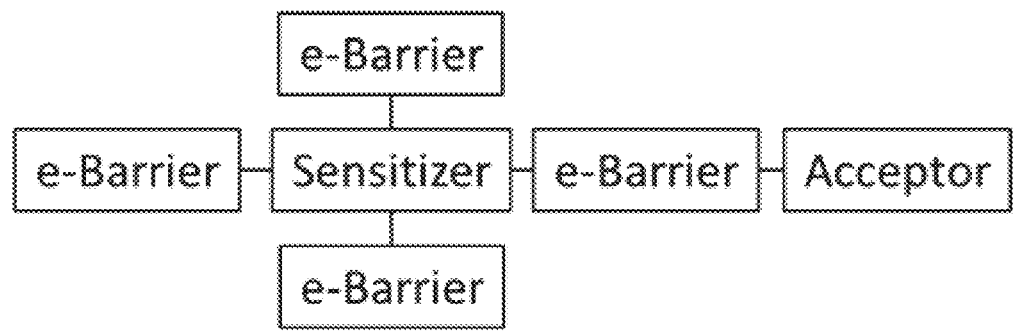

FIG. 4 shows various exemplary molecular design block diagrams according to embodiments of the present invention. Diagram (A) shows a single molecule that includes an acceptor group, a sensitizer group, and an electron-transfer barrier, wherein the electron-transfer barrier is disposed at least partially between the sensitizer group and the acceptor group. Diagram (B) shows a single molecule that includes an acceptor group, a sensitizer group, and an electron-transfer barrier, wherein the electron-transfer barrier substantially surrounds the acceptor group. Diagram (C) shows a single molecule that includes an acceptor group, a sensitizer group, and an electron-transfer barrier, wherein the electron-transfer barrier substantially surrounds the sensitizer group.

In an embodiment, a molecule for organic electroluminescent devices may include a phosphorescent sensitizer group, a fluorescent acceptor group, and an electron-transfer barrier, with the following general structure:

$$S_n\text{—}B_m\text{-}A_y$$

wherein S is a phosphorescent sensitizer group consisting of a transition metal complex, the transition metal complex having at least one ligand or part of a ligand if the ligand is more than bidentate selected from the group consisting of:

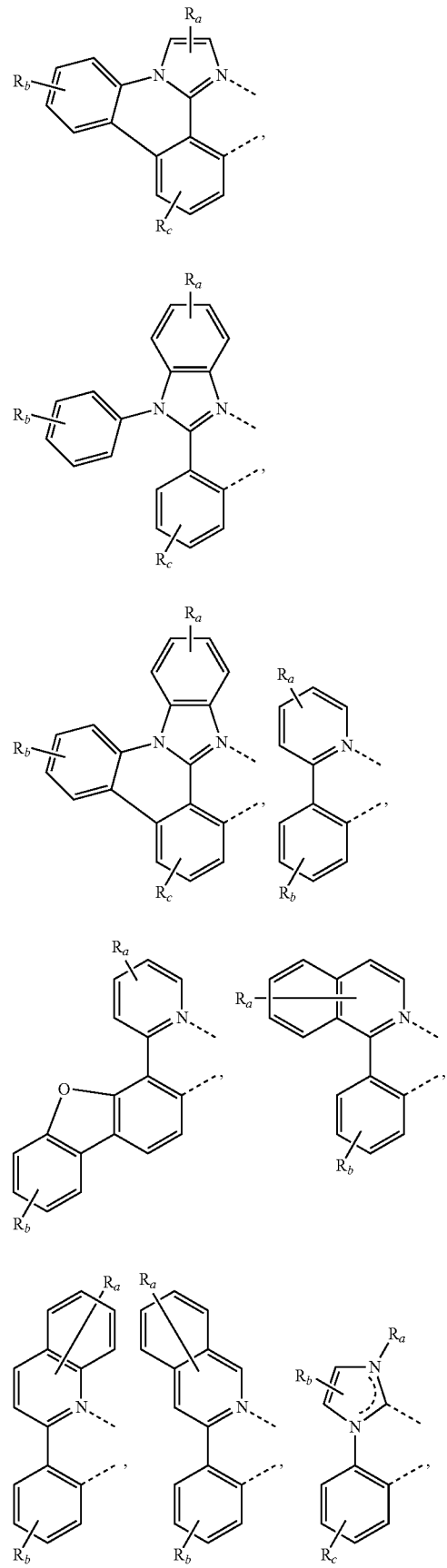

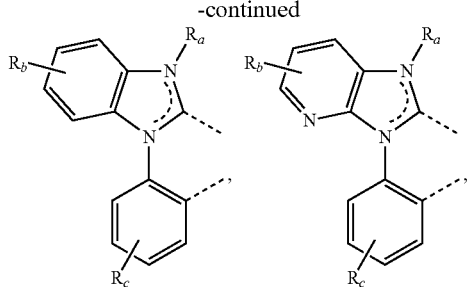
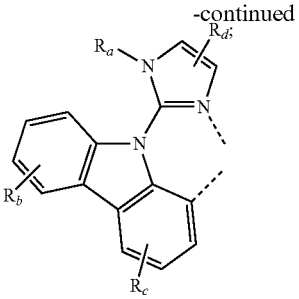

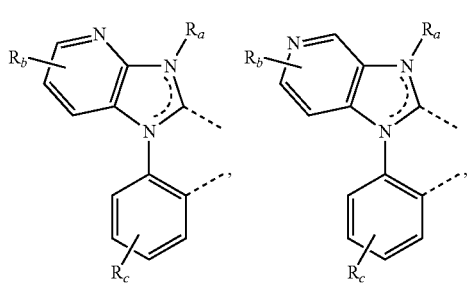

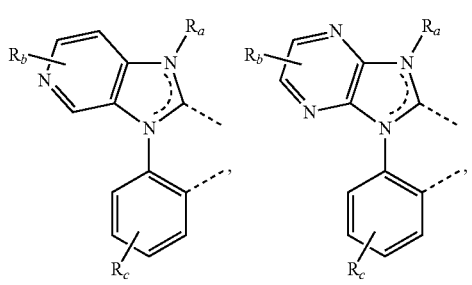

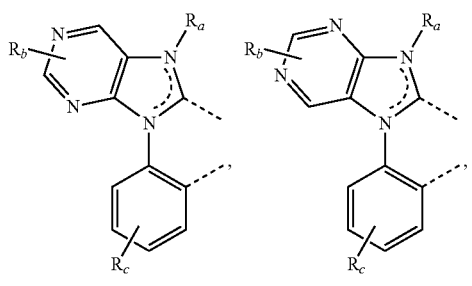

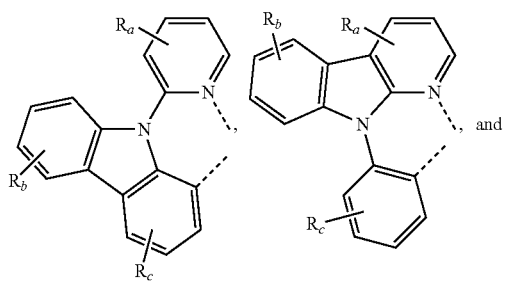 and wherein $R_a$, $R_b$, $R_c$, and $R_d$ may represent mono, di, tri, or tetra substitution, or no substitution; wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of $R_a$, $R_b$, $R_c$, and $R_d$ are optionally joined to form a fused ring or form a multidentate ligand;

n is an integer value of 1 or greater;

B is an electron-transfer barrier group selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, ester, and combinations thereof;

m is an integer value of 1 or greater;

A is a fluorescent acceptor group selected from the group consisting of fluorescent emitting compounds, polycyclic aromatic compounds, naphthalene, anthracene, tetracene, triphylene, pyrene, chrysene, and perylene, and y is an integer value of 1 or greater.

In an embodiment, a molecule for organic electroluminescent devices may include a phosphorescent sensitizer group, a fluorescent acceptor group, and an electron-transfer barrier, with the following general structure:

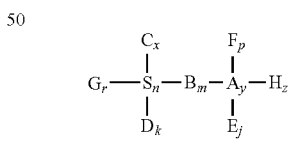

wherein S, A, B, n, m, and y are as described above. Further, each of C, D, E, F, G, and H independently may be an electron-transfer barrier group as described above. Each of x, k, j, p, r, and z independently may be an integer value of 0 or greater. In an embodiment, each of C, D, E, F, G, and H may the same as or different from B and each may be the same as or different from the other C, D, E, F, G, and H.

In an embodiment, examples of the molecules described herein include but are not limited to the following:

TABLE 1
Example Compounds
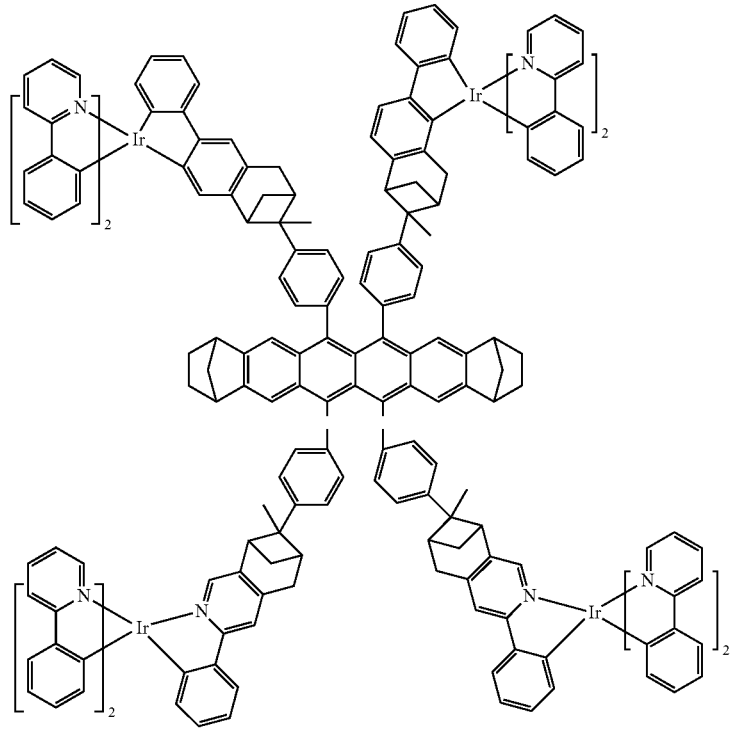
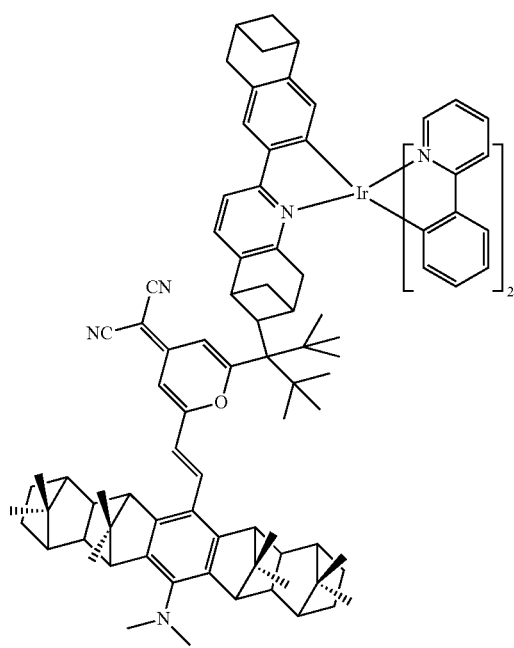

TABLE 1-continued
Example Compounds
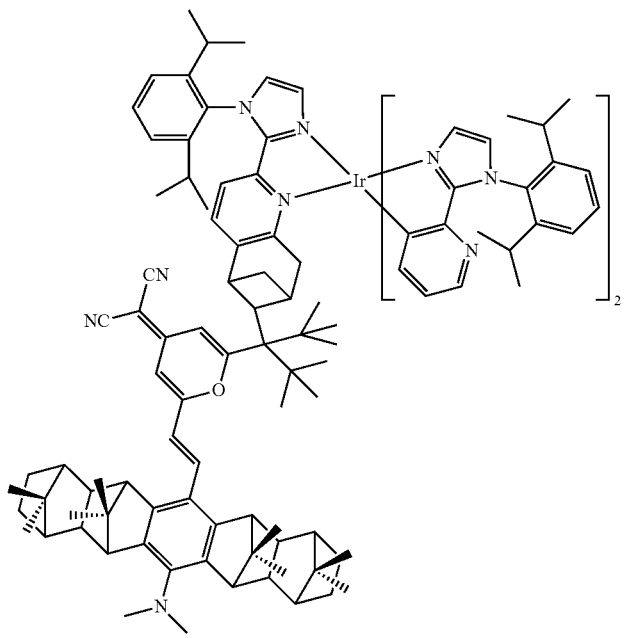
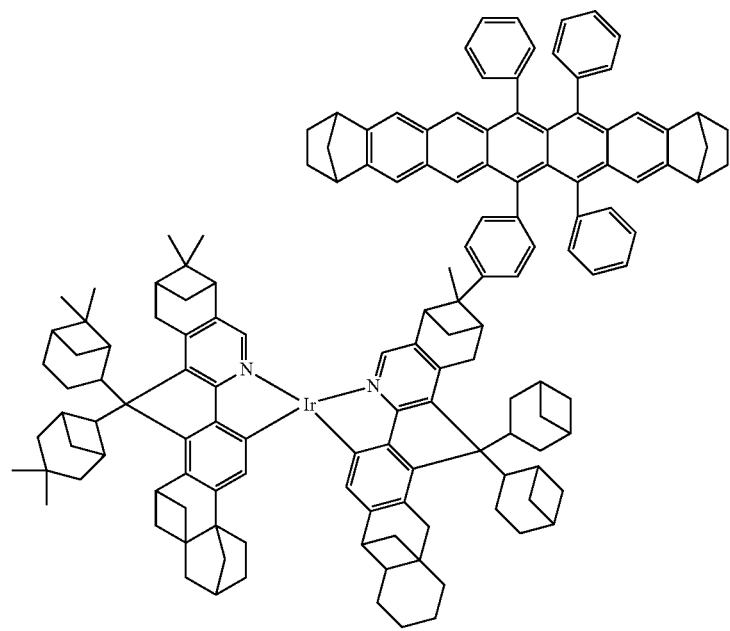

TABLE 1-continued
Example Compounds
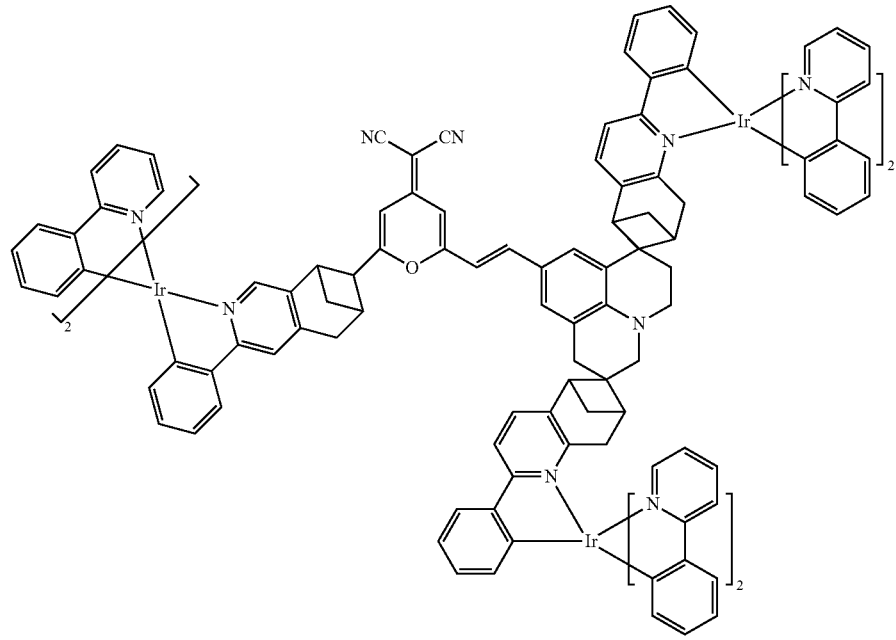
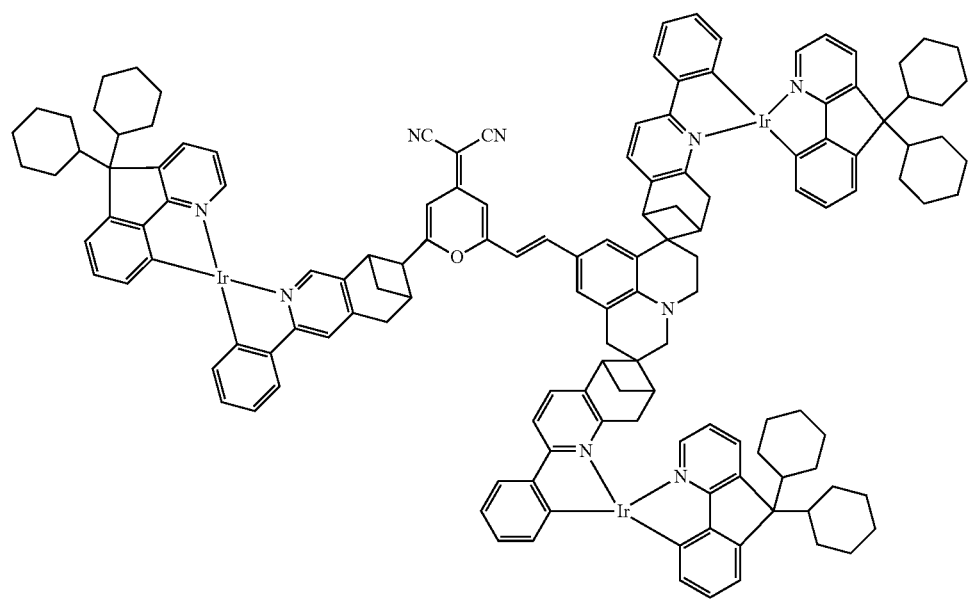

TABLE 1-continued

Example Compounds

[Chemical structure]

In an aspect, an organic light emitting device is also provided. The device includes an anode, a cathode, and an organic emissive layer disposed between the anode and the cathode. The organic emissive layer may include a host and a phosphorescent dopant. In particular, the organic emissive layer may also include a molecule as described above.

The organic light emitting device may include an OLED, a thin film encapsulation layer disposed over or under the OLED, and an active matrix backplane.

A consumer product including a compound as described above is also provided.

In addition to the devices described above, the device may further include a touch sensitive surface. For example, the device may include a component such as a full-color display, a flexible display in a consumer device, a mobile phone, a pad computer, a smartphone, a portable computer, a monitor, a television, and a consumer device including a flexible display.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

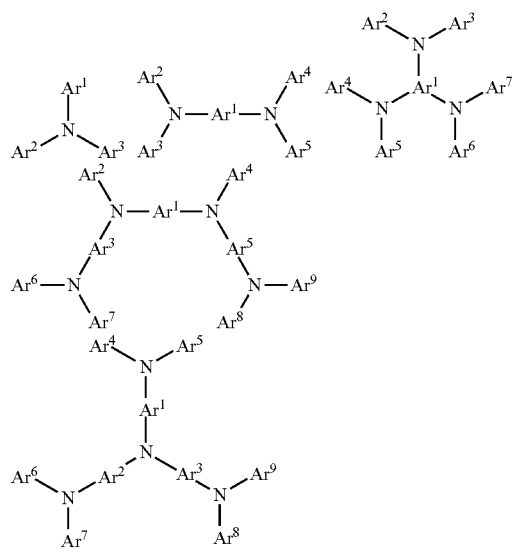

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

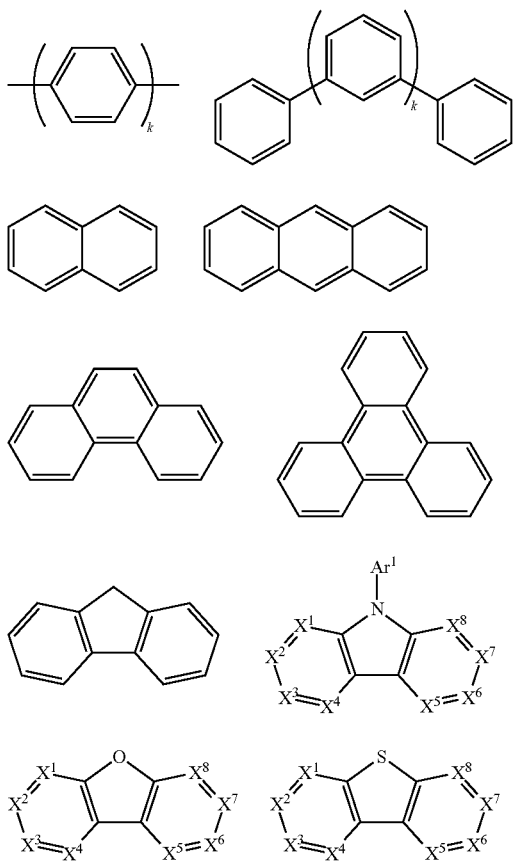

k is an integer from 1 to 20; $X^1$ to $X^8$ is C (including CH) or N; $Ar^1$ has the same group defined above.

Examples of metal complexes used in HIL or HTL include, but not limit to the following general formula:

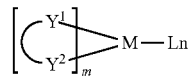

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.
In another aspect, $(Y^1-Y^2)$ is a carbene ligand.
In another aspect, M is selected from Ir, Pt, Os, and Zn.
In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

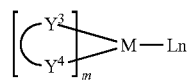

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

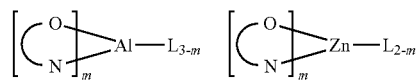

(O—N) is a bidentate ligand, having metal coordinated to atoms O and N.

In another aspect, M is selected from Ir and Pt.
In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

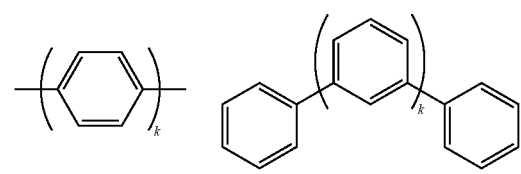
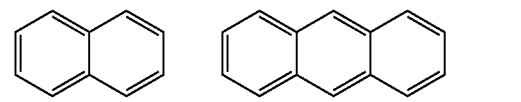
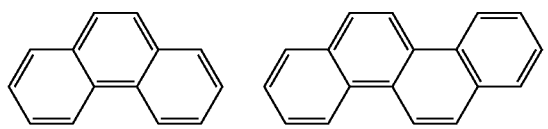
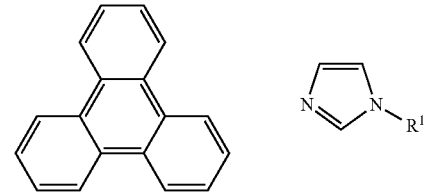
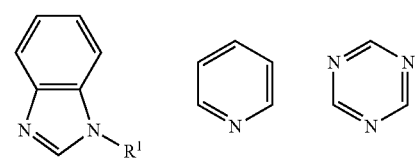
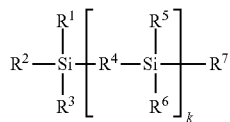

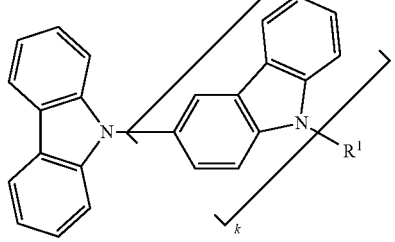
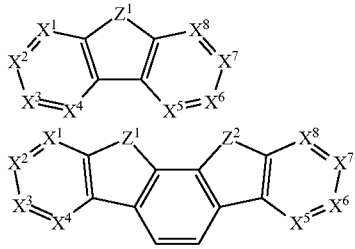
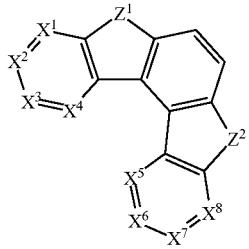
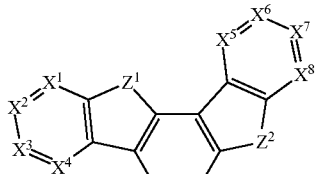
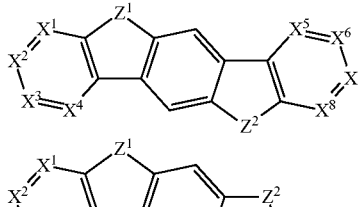

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

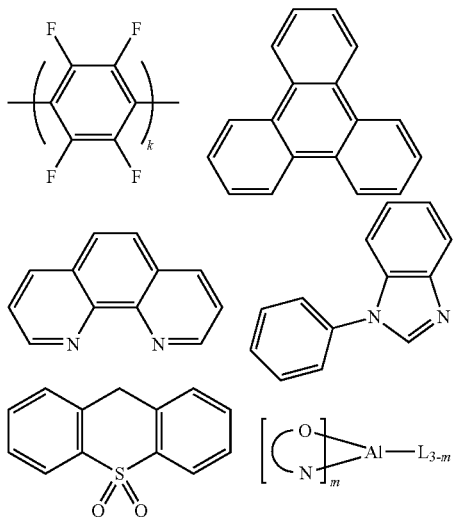

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

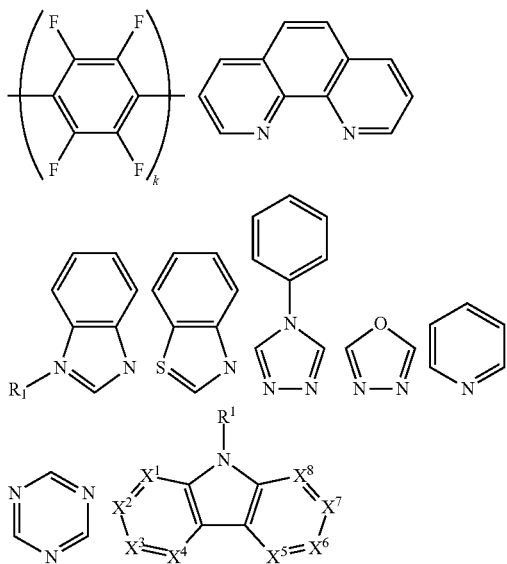

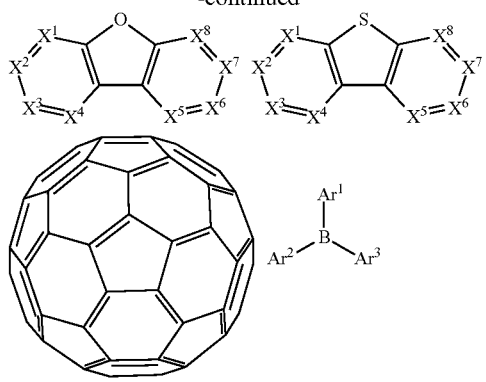

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

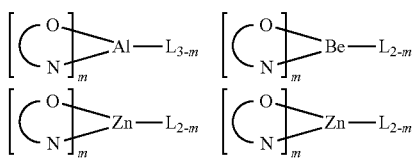

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| Hole injection materials | | |
| Phthalocyanine and porphryin compounds | [Cu phthalocyanine structure] | Appl. Phys. Lett. 69, 2160 (1996) |
| Starburst triarylamines | [starburst triarylamine structure] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | [PEDOT:PSS structure] | Synth. Met. 87, 171 (1997) WO2007002683 |
| Phosphonic acid and sliane SAMs | $N{-}(C_6H_4{-}SiCl_3)_3$ | US20030162053 |

TABLE 2-continued
| MATERIAL | EXAMPLES OF MATERIAL | PUBLICATIONS |
|---|---|---|
| Triarylamine or polythiophene polymers with conductivity dopants | 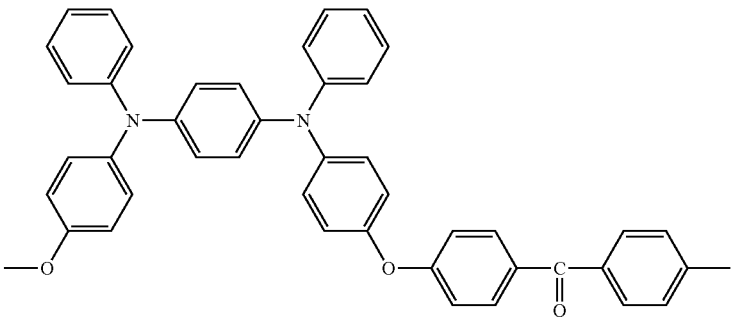 and 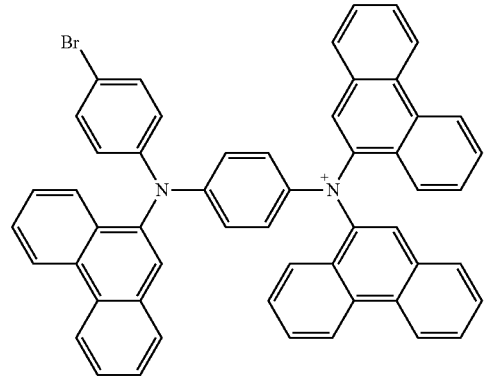 [SMILES: Brc1ccc(N(c2ccc(N(c3cc4ccccc4c4ccccc34)c3cc4ccccc4c4ccccc34)cc2)c2cc3ccccc3c3ccccc23)cc1] 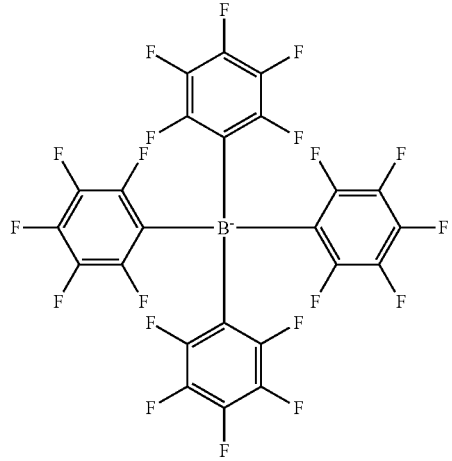 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 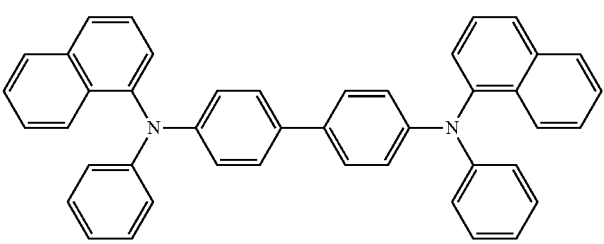 + MoO$_x$ | US20050123751 SID Symposium Digest, 37, 923 (2006) WO2009018009 |

TABLE 2-continued
| MATERIAL | EXAMPLES OF MATERIAL | PUBLICATIONS |
| --- | --- | --- |
| n-type semiconducting organic complexes | 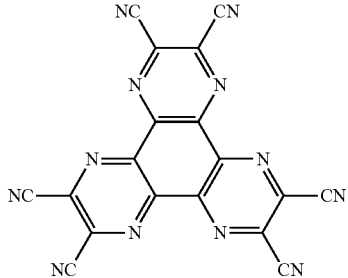 [SMILES: N#Cc1nc2c3nc(C#N)c(C#N)nc3c3nc(C#N)c(C#N)nc3c2nc1C#N] | US20020158242 |
| Metal organometallic complexes | 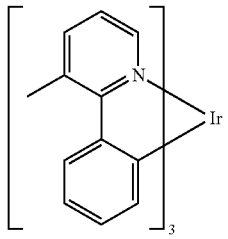 | US20060240279 |
| Cross-linkable compounds | 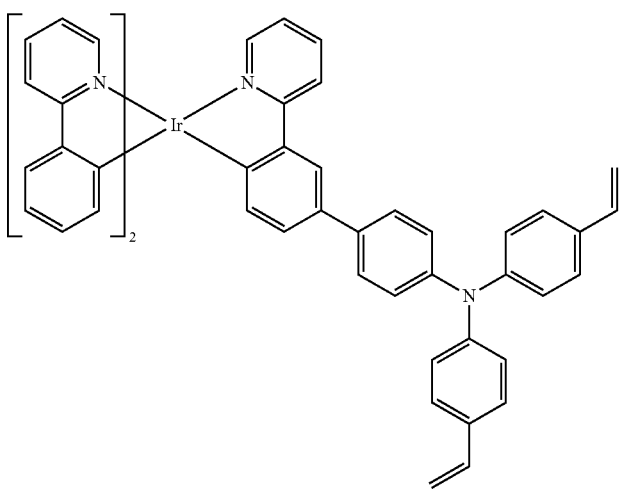 | US20080220265 |
| Polythiophene based polymers and copolymers | 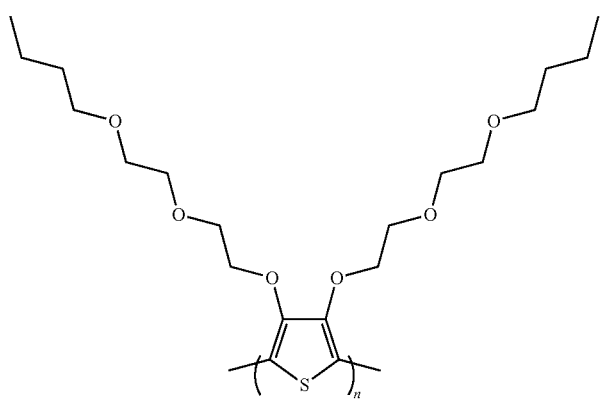 | WO 2011075644<br>EP2350216 |

TABLE 2-continued
| MATERIAL | EXAMPLES OF MATERIAL | PUBLICATIONS |
| --- | --- | --- |
| Hole transporting materials | | |
| Triarylamines (e.g., TPD, □-NPD) | 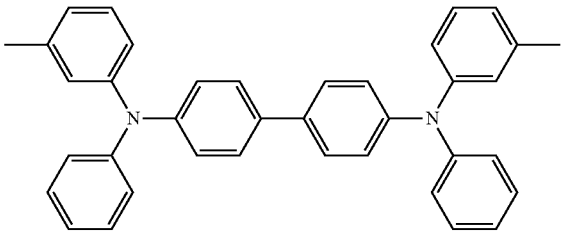 | Appl. Phys. Lett. 51, 913 (1987) |
| | 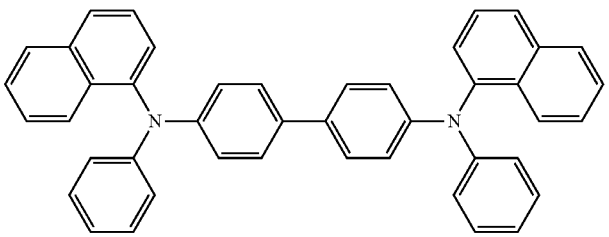 [SMILES: c1ccc(N(c2ccc(-c3ccc(N(c4ccccc4)c4cccc5ccccc45)cc3)cc2)c2cccc3ccccc23)cc1] | US5061569 |
| | 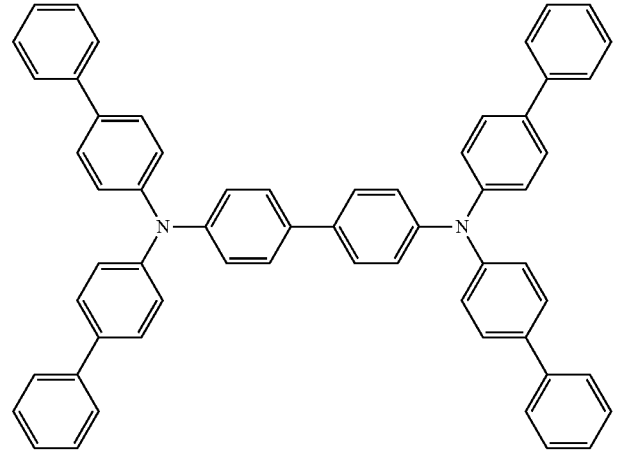 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 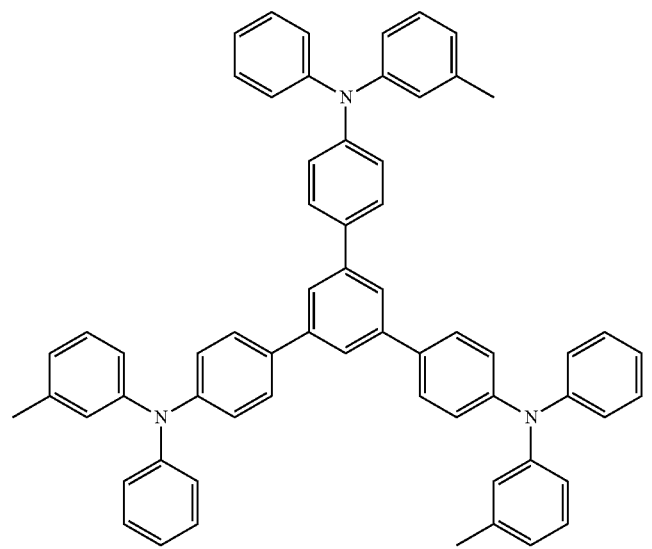 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 2-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 2-continued
| MATERIAL | EXAMPLES OF MATERIAL | PUBLICATIONS |
|---|---|---|
| Triarylamine with (di)benzothiophene/ (di)benzofuran | 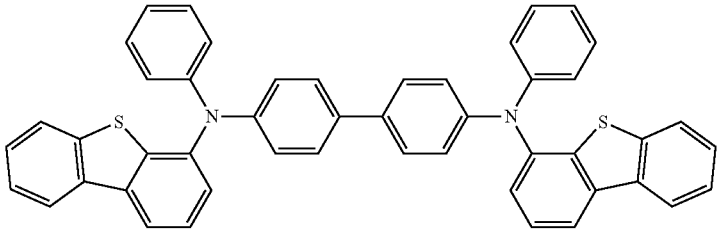 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 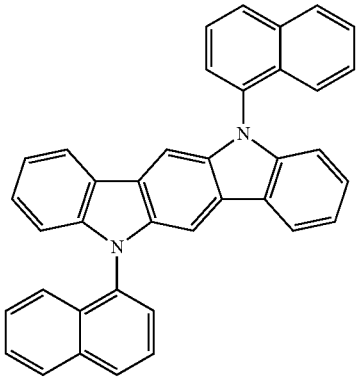 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 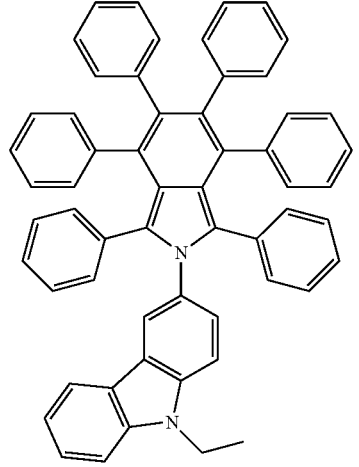 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 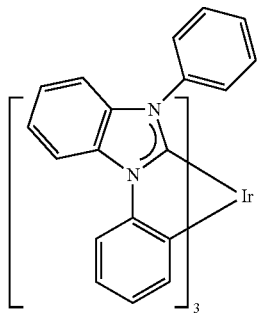 | US20080018221 |

TABLE 2-continued

| MATERIAL | EXAMPLES OF MATERIAL | PUBLICATIONS |
| --- | --- | --- |
| Phosphorescent OLED host materials | | |
| Red hosts | | |
| Arylcarbazoles | [structure] | Appl. Phys. Lett. 78, 1622 (2001) |
| Metal 8-hydroxyquinolates (e.g., Alq$_3$, BAlq) | [structure] | Nature 395, 151 (1998) |
| | [structure] | US20060202194 |
| | [structure] | WO2005014551 |
| | [structure] | WO2006072002 |
| Metal phenoxybenzothiazole compounds | [structure] | Appl. Phys. Lett. 90, 123509 (2007) |
| Conjugated oligomers and polymers (e.g., polyfluorene) | [structure] | Org. Electron. 1, 15 (2000) |

TABLE 2-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| | Green hosts | |
| Arylcarbazoles | | Appl. Phys. Lett. 78, 1622 (2001) |
| | | US20030175553 |
| | | WO2001039234 |

TABLE 2-continued
| MATERIAL | EXAMPLES OF MATERIAL | PUBLICATIONS |
|---|---|---|
| Aryltriphenylene compounds | 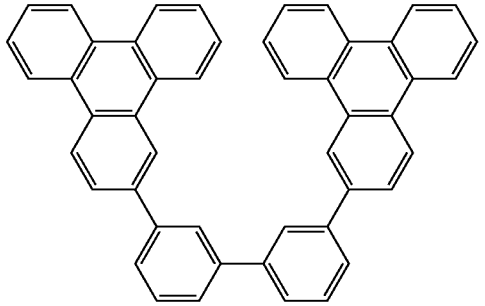 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 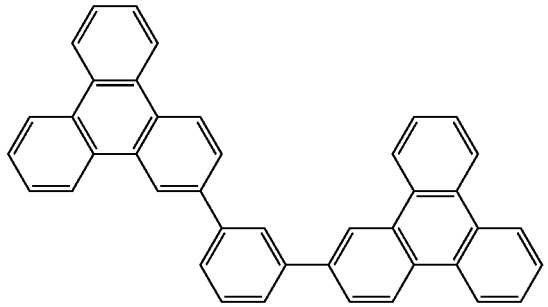 [SMILES: c1cc(-c2ccc3c4ccccc4c4ccccc4c3c2)cc(-c2ccc3c4ccccc4c4ccccc4c3c2)c1] | US20060280965 |
| | 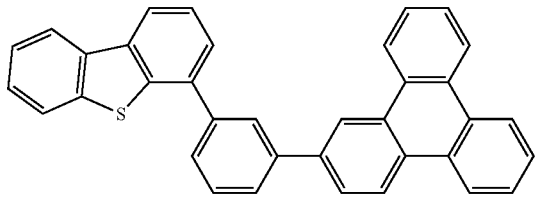 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 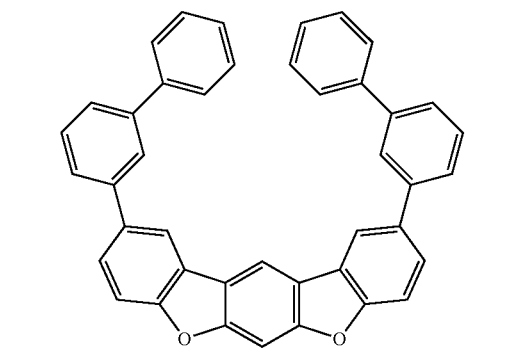 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 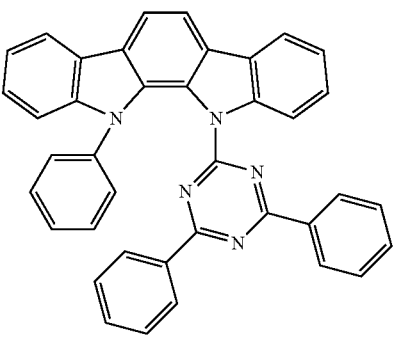 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 2-continued

| MATERIAL | EXAMPLES OF MATERIAL | PUBLICATIONS |
| --- | --- | --- |
| | | WO2010107244 |
| Aza-carbazole/ DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |

TABLE 2-continued

| MATERIAL | EXAMPLES OF MATERIAL | PUBLICATIONS |
|---|---|---|
| Metal phenoxy-benzooxazole compounds | | WO2005089025 |
| | | WO2006132173 |
| | | JP200511610 |
| Spirofluorene-carbazole compounds | | JP2007254297 |
| | | JP2007254297 |

TABLE 2-continued

| MATERIAL | EXAMPLES OF MATERIAL | PUBLICATIONS |
| --- | --- | --- |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 2-continued
| MATERIAL | EXAMPLES OF MATERIAL | PUBLICATIONS |
|---|---|---|
| | 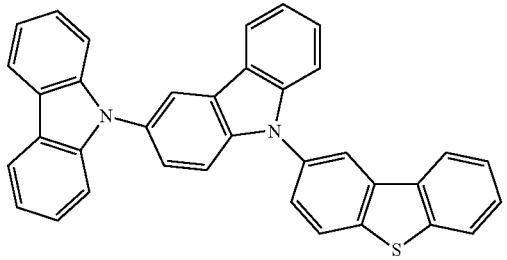 [SMILES: c1ccc2c(c1)sc1ccc(-n3c4ccccc4c4cc(-n5c6ccccc6c6ccccc65)ccc43)cc12] | WO2009086028 |
| | 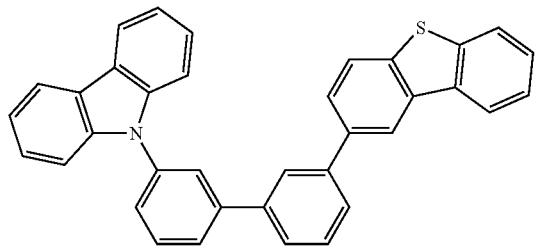 [SMILES: c1cc(-c2cccc(-n3c4ccccc4c4ccccc43)c2)cc(-c2ccc3sc4ccccc4c3c2)c1] | US20090030202, US20090017330 |
| | 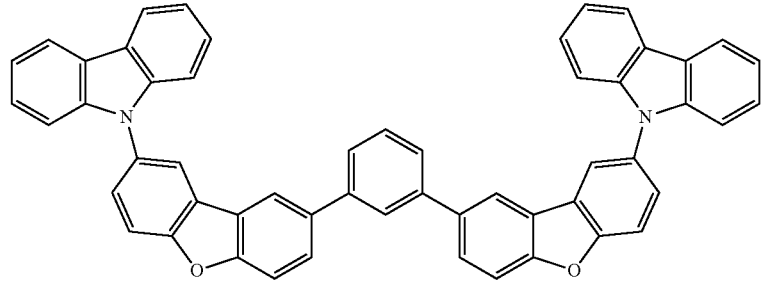 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 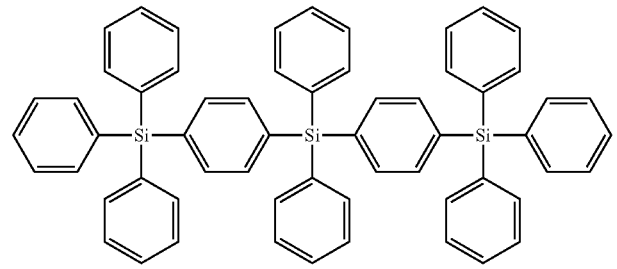 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 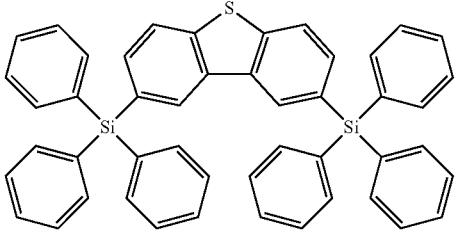 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE 2-continued

| MATERIAL | EXAMPLES OF MATERIAL | PUBLICATIONS |
| --- | --- | --- |
| | Phosphorescent dopants | |
| | Red dopants | |
| Heavy metal porphyrins (e.g., PtOEP) | [structure of PtOEP with eight ethyl substituents] | Nature 395, 151 (1998) |
| Iridium(III) organometallic complexes | [Ir complex with benzothienylpyridine and acac ligands] | Appl. Phys. Lett. 78, 1622 (2001) |
| | [Ir complex with phenylisoquinoline and acac ligands] | US2006835469 |
| | [Ir complex with methylquinoline-phenyl and acac ligands] | US2006835469 |
| | [Ir complex with substituted quinoline-phenyl and acac ligands] | US20060202194 |

TABLE 2-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater. 19, 739 (2007) |

| MATERIAL | EXAMPLES OF MATERIAL | PUBLICATIONS |
|---|---|---|
| | [Ir(acac) complex with substituted dibenzo[f,h]quinoxaline ligand bearing two phenyl groups] | WO2009100991 |
| | [Ir(acac) complex with 1-(benzotriazol-2-yl)naphthalene ligand] | WO2008101842 |
| | [Ir complex with biphenyl, two PPh₃ and Cl ligands] | U.S. Pat. No. 7,232,618 |
| Platinum(II) organometallic complexes | [Pt complex with 1-phenylisoquinoline and acac ligands] | WO2003040257 |
| | [Pt complex with bis(pyridylphenyl)amine tridentate ligand, N-phenyl] | US20070103060 |

TABLE 2-continued
| MATERIAL | EXAMPLES OF MATERIAL | PUBLICATIONS |
| --- | --- | --- |
| Osminum(III) complexes | 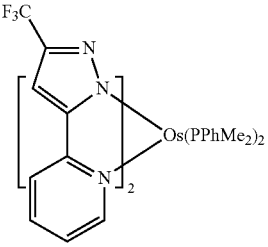 | Chem. Mater. 17, 3532 (2005) |
| Ruthenium(II) complexes | 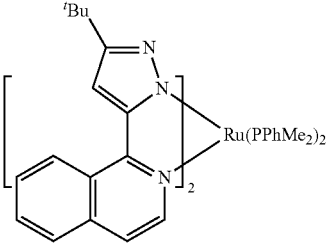 | Adv. Mater. 17, 1059 (2005) |
| Rhenium (I), (II), and (III) complexes | 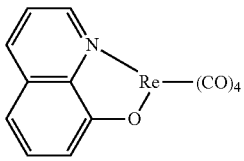 | US20050244673 |
| | Green dopants | |
| Iridium(III) organometallic complexes | 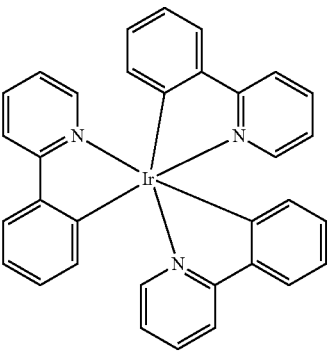<br>and its derivatives | Inorg. Chem. 40, 1704 (2001) |
| | 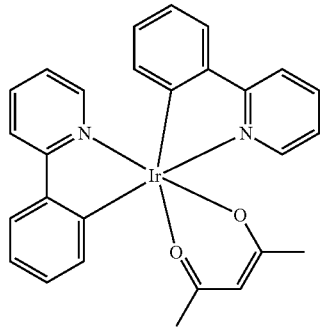 | US20020034656 |

TABLE 2-continued
| MATERIAL | EXAMPLES OF MATERIAL | PUBLICATIONS |
|---|---|---|
| | 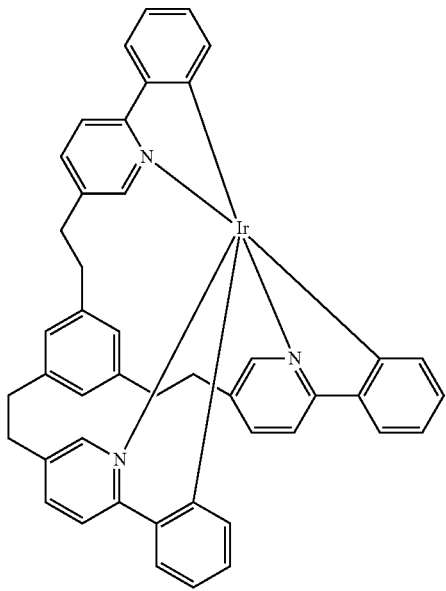 | U.S. Pat. No. 7,332,232 |
| | 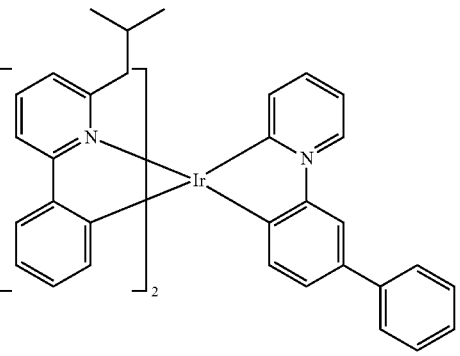 | US20090108737 |
| | 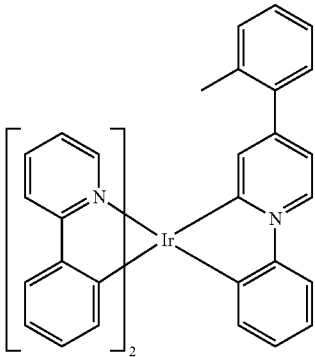 | WO2010028151 |

TABLE 2-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE 2-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670 JP2007123392 |
| | | WO2010086089, WO2011044988 |
| | | Adv. Mater. 16, 2003 (2004) |

TABLE 2-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 2-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 2-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 2-continued
| MATERIAL | EXAMPLES OF MATERIAL | PUBLICATIONS |
|---|---|---|
| Gold complexes | 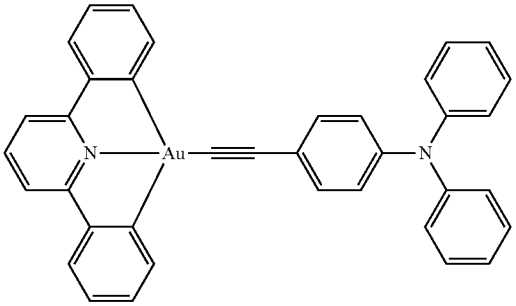 | Chem. Commun. 2906 (2005) |
| Rhenium(III) complexes | 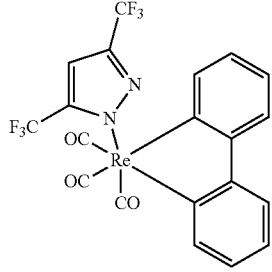 | Inorg. Chem. 42, 1248 (2003) |
| Osmium(II) complexes | 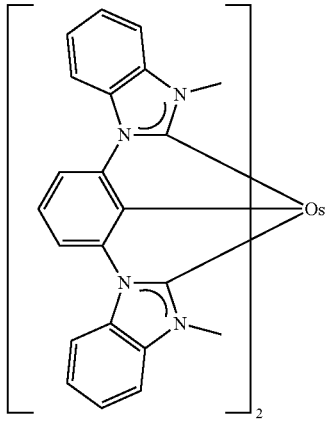 | U.S. Pat. No. 7,279,704 |
| Deuterated organometallic complexes | 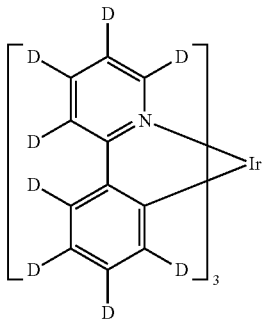 | US20030138657 |

TABLE 2-continued
| MATERIAL | EXAMPLES OF MATERIAL | PUBLICATIONS |
|---|---|---|
| Organometallic complexes with two or more metal centers | 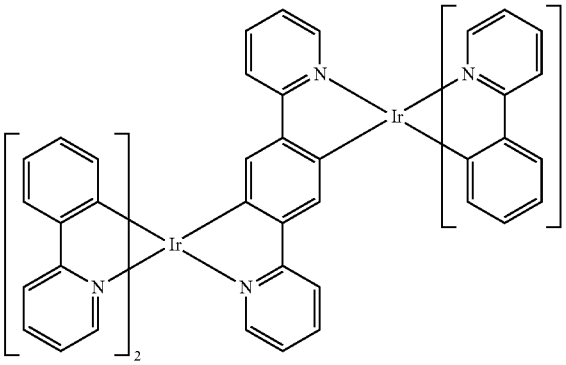 | US20030152802 |
| | 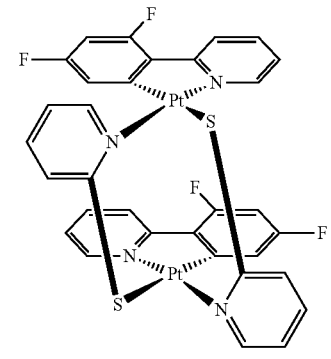 | U.S. Pat. No. 7,090,928 |
| | Blue dopants | |
| Iridium(III) organometallic complexes | 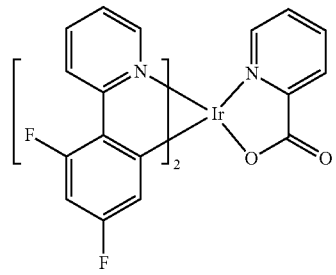 | WO2002002714 |
| | 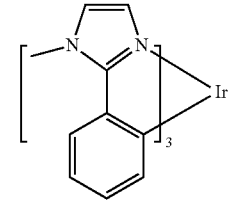 | WO2006009024 |
| | 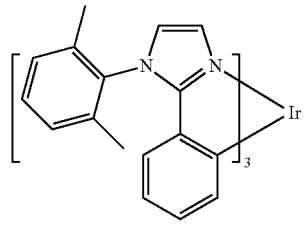 | US20060251923<br>US20110057559<br>US20110204333 |

TABLE 2-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 2-continued
| MATERIAL | EXAMPLES OF MATERIAL | PUBLICATIONS |
|---|---|---|
| | 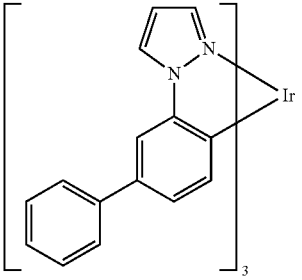 | U.S. Pat. No. 7,338,722 |
| | 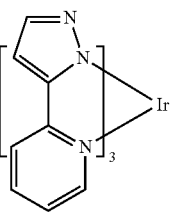 | US20020134984 |
| | 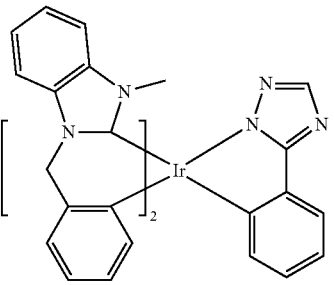 | Angew. Chem. Int. Ed. 47, 1 (2008) |
| | 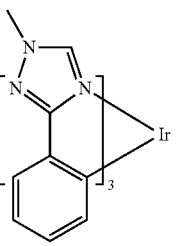 | Chem. Mater. 18, 5119 (2006) |
| | 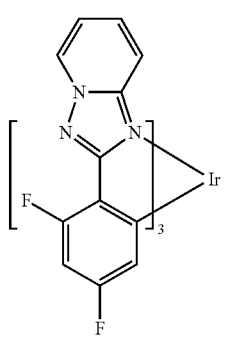 | Inorg. Chem. 46, 4308 (2007) |

TABLE 2-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 2-continued

| MATERIAL | EXAMPLES OF MATERIAL | PUBLICATIONS |
|---|---|---|
| | 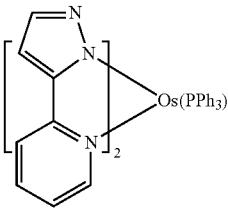 | Organometallics 23, 3745 (2004) |
| Gold complexes | 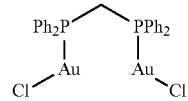 | Appl. Phys. Lett. 74, 1361 (1999) |
| Platinum(II) complexes | 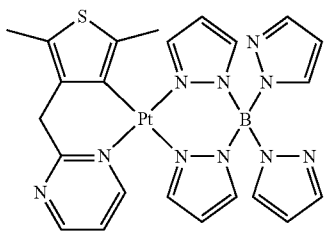 | WO2006098120, WO2006103874 |
| Pt tetradentate complexes with at least one metal-carbene bond | 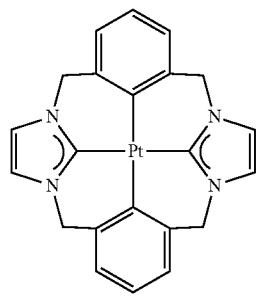 | U.S. Pat. No. 7,655,323 |
| Exciton/hole blocking layer materials | | |
| Bathocuprine compounds (e.g., BCP, BPhen) | 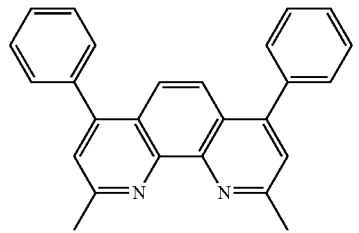 [SMILES: Cc1cc(-c2ccccc2)c2ccc3c(-c4ccccc4)cc(C)nc3c2n1] | Appl. Phys. Lett. 75, 4 (1999) |
| | 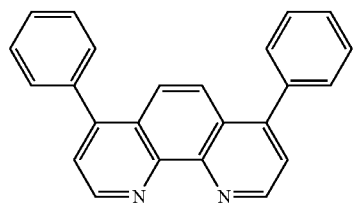 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 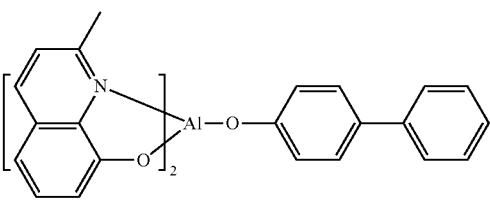 | Appl. Phys. Lett. 81, 162 (2002) |

TABLE 2-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 2-continued
| MATERIAL | EXAMPLES OF MATERIAL | PUBLICATIONS |
|---|---|---|
| Phenothiazine-S-oxide | 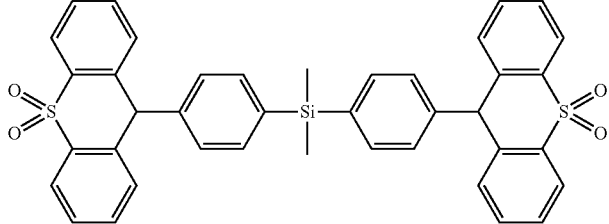 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 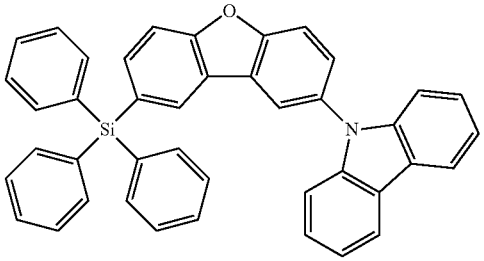 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 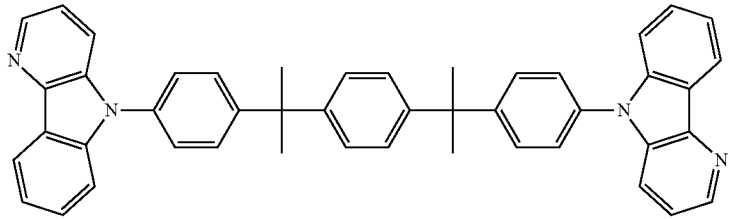 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 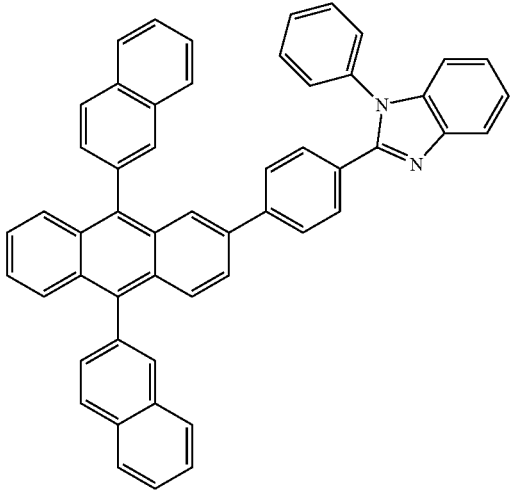 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 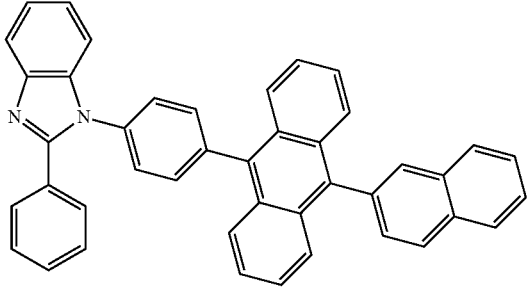 [SMILES: c1ccc(-c2nc3ccccc3n2-c2ccc(-c3c4ccccc4c(-c4ccc5ccccc5c4)c4ccccc34)cc2)cc1] | US20090179554 |

TABLE 2-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 2-continued
| MATERIAL | EXAMPLES OF MATERIAL | PUBLICATIONS |
|---|---|---|
| 5-member ring electron deficient heterocycles (e.g.,triazole, oxadiazole, imidazole, benzoimidazole) | 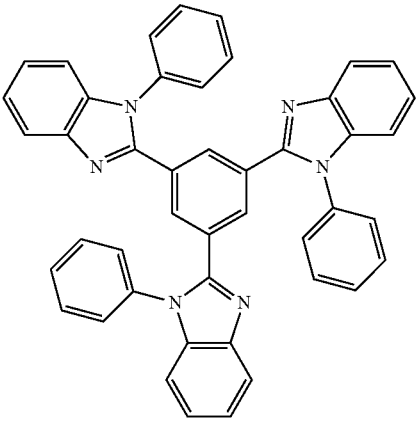 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 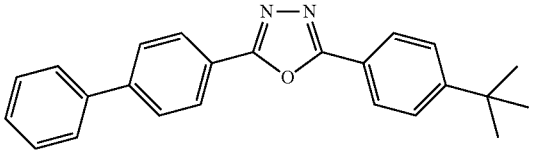 [SMILES: CC(C)(C)c1ccc(-c2nnc(-c3ccc(-c4ccccc4)cc3)o2)cc1] | Appl. Phys. Lett. 55, 1489 (1989) |
| | 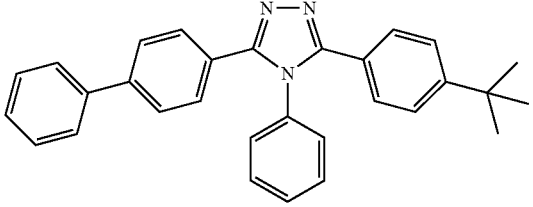 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 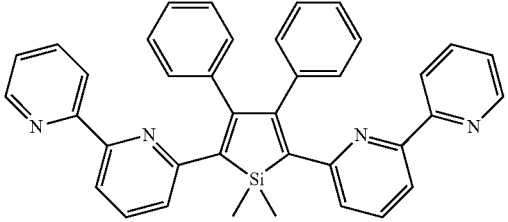 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 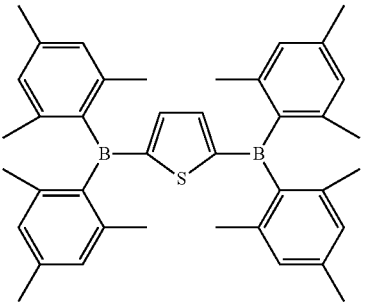 | J. Am. Chem. Soc. 120, 9714 (1998) |
| Fluorinated aromatic compounds | 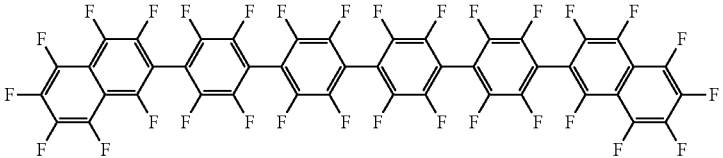 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 2-continued

| MATERIAL | EXAMPLES OF MATERIAL | PUBLICATIONS |
|---|---|---|
| Fullerene (e.g., C60) | 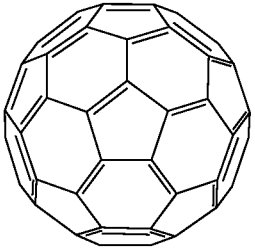 | US20090101870 |
| Triazine complexes | 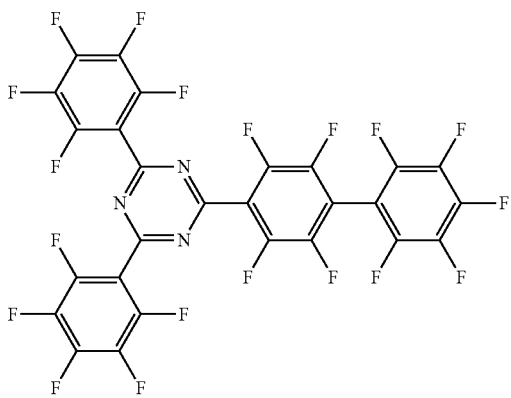 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 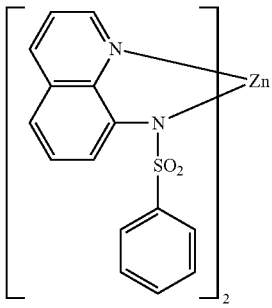 | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A molecule comprising:
   a sensitizer group, comprising a metal containing phosphorescent moiety;
   an acceptor group, and
   an electron-transfer barrier that suppresses triplet-triplet energy transfer between the sensitizer group and the acceptor group, the electron transfer barrier being a cycloalkyl group.

2. The molecule of claim 1, wherein the maximum length of the electron-transfer barrier is about 10 nm.

3. The molecule of claim 1, wherein the maximum length of the electron-transfer barrier is about 8 nm.

4. The molecule of claim 1, wherein the acceptor group comprises a fluorescent moiety.

5. The molecule of claim 4, wherein the acceptor group comprises a poly-aromatic moiety.

6. The molecule of claim 4, wherein the acceptor group comprises a quantum dot.

7. The molecule of claim 1, wherein the electron-transfer barrier is disposed at least partially between the sensitizer group and the acceptor group.

8. The molecule of claim 1, wherein the electron-transfer barrier substantially surrounds the acceptor group.

9. The molecule of claim 1, wherein the electron-transfer barrier substantially surrounds the sensitizer group.

10. A device comprising an organic layer comprising a molecule of claim 1.

11. The device of claim 10, wherein the device comprises an OLED.

12. The device of claim 11, further comprising a thin film encapsulation layer disposed over or under the OLED.

13. The device of claim 10, further comprising:
an anode; and
a cathode;
wherein the organic layer is disposed between the anode and the cathode.

14. The device of claim 10, further comprising a touch sensitive surface.

15. The device of claim 10, wherein the device comprises a device type selected from the group consisting of: a full-color display, a flexible display in a consumer device, a mobile phone, a pad computer, a smartphone, a portable computer, a monitor, a television, and a consumer device including a flexible display.

16. The device of claim 10, wherein the device comprises an active matrix backplane.

17. A consumer product comprising the molecule of claim 1.

18. A molecule for organic electroluminescent devices comprising:
a phosphorescent sensitizer group, comprising a metal containing phosphorescent moiety;
a fluorescent acceptor group, and
an electron-transfer barrier;
the molecule having a structure of:

wherein S is a phosphorescent sensitizer group;
n is an integer value of 1 or greater;
B is an electron-transfer barrier group that is a cycloalkyl group;
m is an integer value of 1 or greater;
A is a fluorescent acceptor group selected from the group consisting of fluorescent emitting compounds, polycyclic aromatic compounds, naphthalene, anthracene, tetracene, triphenylene, pyrene, chrysene, and perylene, and
y is an integer value of 1 or greater.

19. The molecule of claim 18, wherein the phosphorescent sensitizer group is a transition metal complex, the transition metal complex having at least one ligand or part of a ligand if the ligand is more than bidentate selected from the group consisting of:

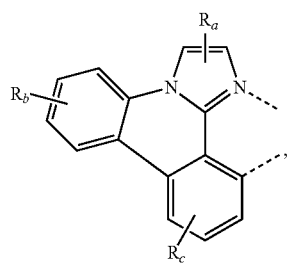

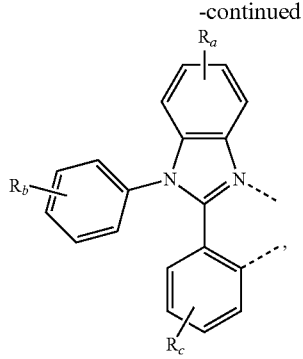

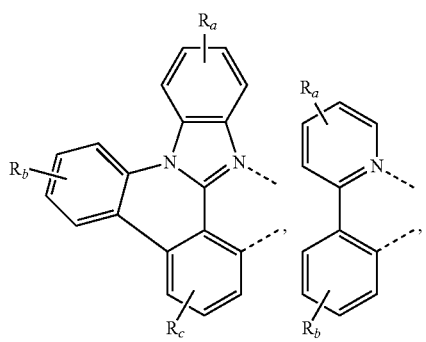

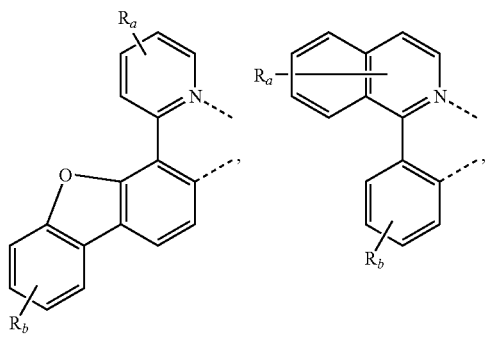

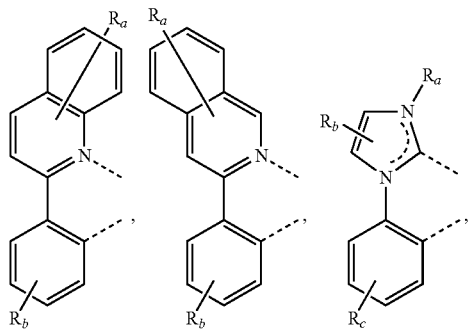

-continued

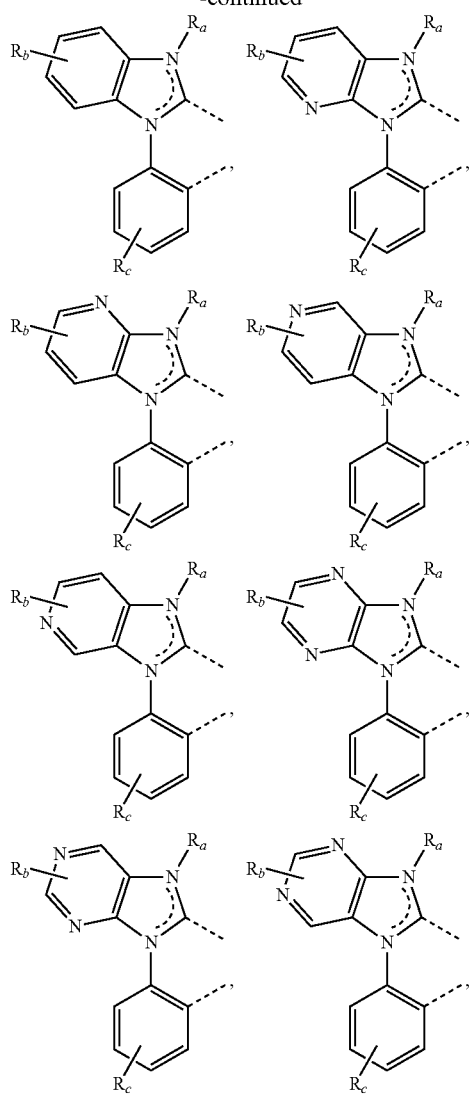

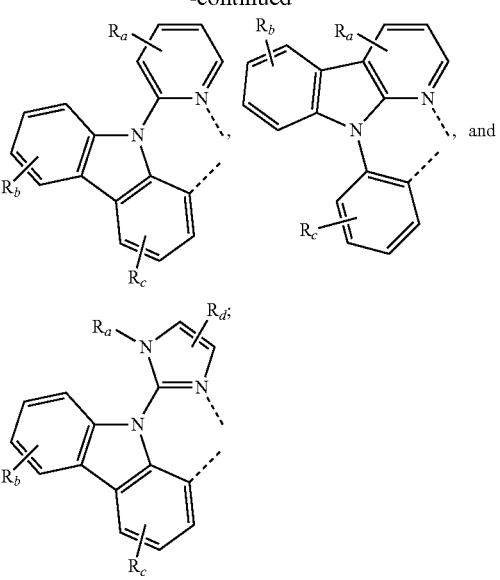

wherein Ra, Rb, Rc, and Rd may represent mono, di, tri, or tetra substitution, or no substitution; wherein Ra, Rb, Rc, and Rd are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of Ra, Rb, Rc, and Rd are optionally joined to form a fused ring or form a multidentate ligand.

20. A device comprising an organic layer comprising a molecule of claim 18.

21. A consumer product comprising the molecule of claim 18.

22. A compound selected from the group consisting of:

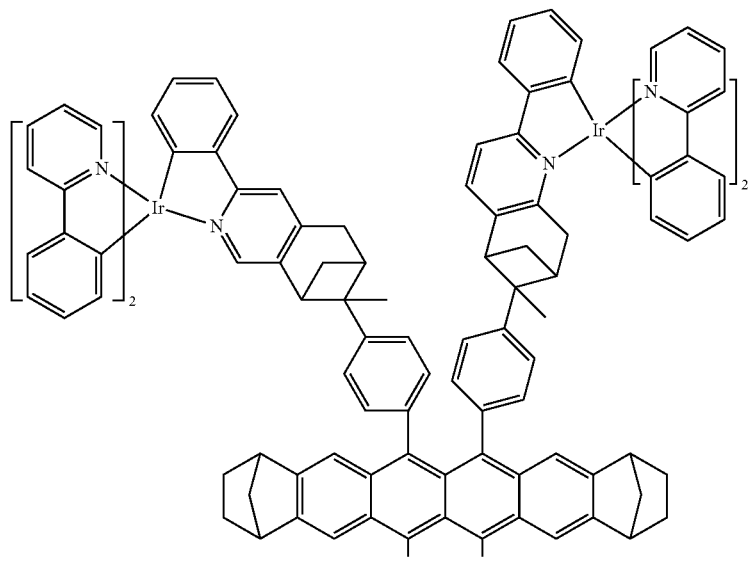

-continued
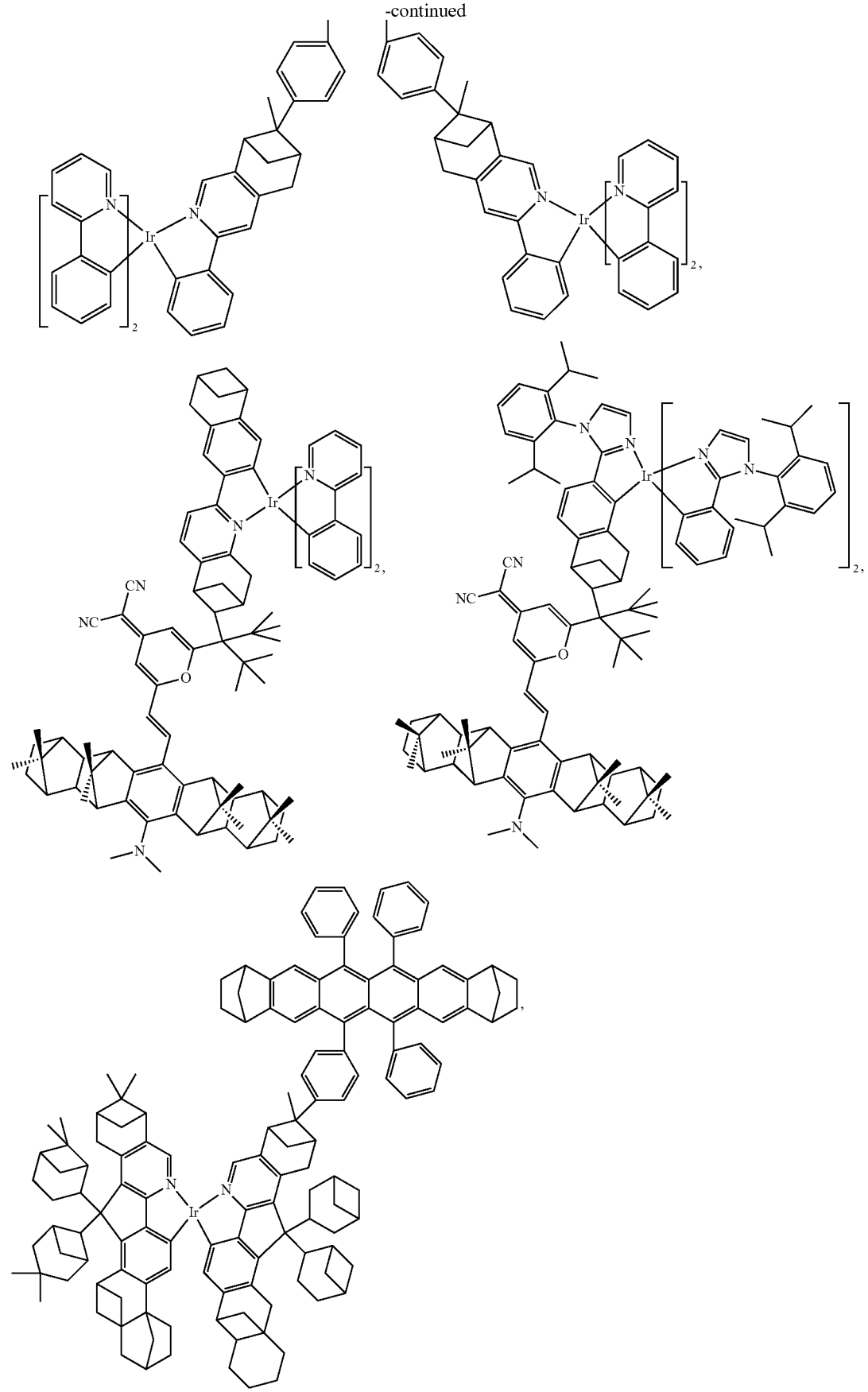

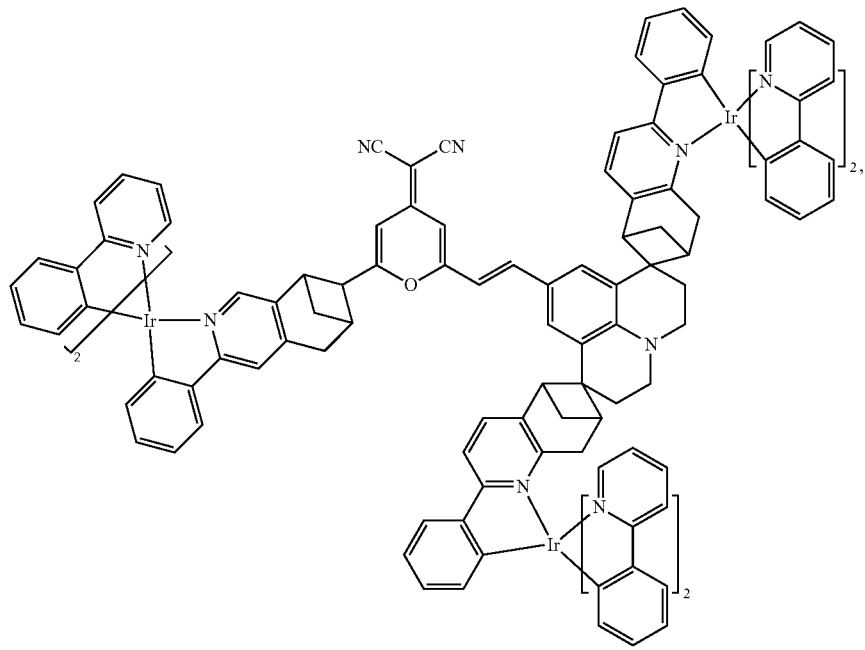
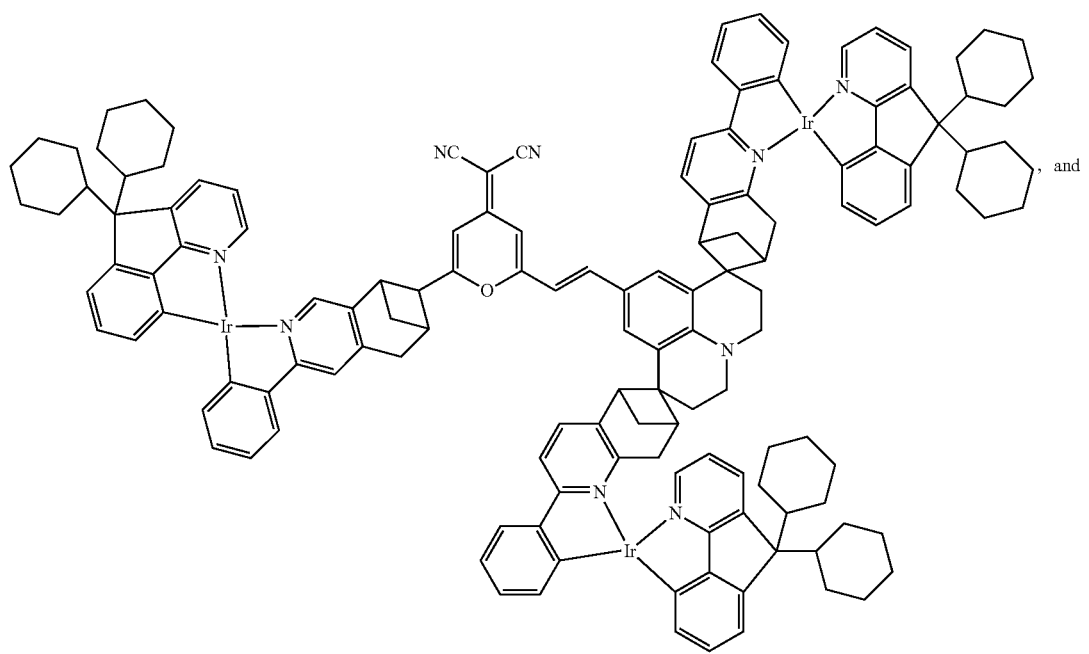

-continued
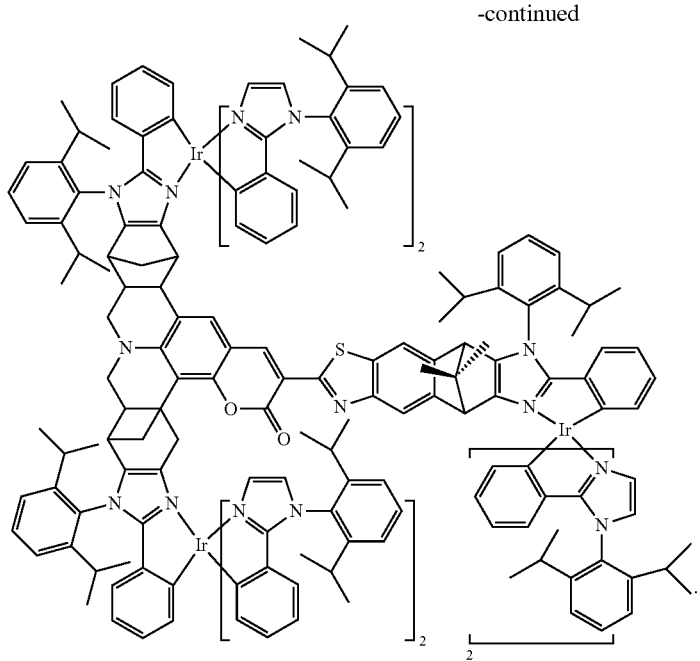
23. An organic light emitting device comprising:
an anode;
a cathode, and
an organic layer, disposed between the anode and the cathode, the organic layer comprising a compound as recited in claim 22.
* * * * *